(12) United States Patent
Sohn et al.

(10) Patent No.: US 8,707,787 B1
(45) Date of Patent: Apr. 29, 2014

(54) TIME DELAY BASED HEALTH MONITORING SYSTEM USING A SENSOR NETWORK

(75) Inventors: Hoon Sohn, Seoul (KR); Chul Min Yeum, Cheongju (KR); Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 355 days.

(21) Appl. No.: 13/084,276

(22) Filed: Apr. 11, 2011

Related U.S. Application Data

(60) Provisional application No. 61/449,577, filed on Mar. 4, 2011.

(51) Int. Cl.
*G01N 29/07* (2006.01)

(52) U.S. Cl.
USPC .................................. 73/602; 73/597; 73/620

(58) Field of Classification Search
USPC ........... 73/602, 596, 618, 620, 625, 627, 628, 73/633, 597; 702/35, 36, 39, 159
See application file for complete search history.

(56) References Cited

U.S. PATENT DOCUMENTS

| | | | | |
|---|---|---|---|---|
| 5,431,054 | A * | 7/1995 | Reeves et al. ............ | 73/612 |
| 5,563,346 | A * | 10/1996 | Bartelt et al. ............ | 73/626 |
| 6,996,480 | B2 * | 2/2006 | Giurgiutiu et al. ........... | 702/35 |
| 7,286,964 | B2 | 10/2007 | Kim | |
| 7,333,898 | B2 | 2/2008 | Griess et al. | |
| 7,596,470 | B2 | 9/2009 | Kim | |
| 7,743,659 | B2 * | 6/2010 | Kearns et al. ............ | 73/632 |
| 7,822,573 | B2 | 10/2010 | Ihn | |
| 7,881,881 | B2 * | 2/2011 | Giurgiutiu et al. ........... | 702/39 |
| 7,917,311 | B2 * | 3/2011 | Finkel et al. ............ | 702/39 |
| 7,921,727 | B2 | 4/2011 | Rice | |
| 7,991,587 | B2 | 8/2011 | Ihn | |
| 8,286,490 | B2 * | 10/2012 | Ruzzene et al. ............ | 73/618 |
| 8,286,492 | B2 | 10/2012 | Sohn et al. | |
| 2007/0265808 | A1 | 11/2007 | Kim | |
| 2012/0255359 | A1 | 10/2012 | Sohn et al. | |

FOREIGN PATENT DOCUMENTS

GB     2451959 A     2/2009

OTHER PUBLICATIONS

Petculescu et al., "Group delay measurements using modally selective Lamb wave transduceers for detection and sizing of delaminations in composites", Smart Materials and Structures, 17 (2008) pp. 1-9.

Sohn, "Effects of environmental and operational variability on structural health monitoring", Philosophical Transactions of The Royal Society, 2007, pp. 1-23.

(Continued)

*Primary Examiner* — J M Saint Surin
(74) *Attorney, Agent, or Firm* — Yee & Associates, P.C.

(57) ABSTRACT

A method and apparatus for detecting an inconsistency in an object. Signals sent on a plurality of paths in the object are received at a plurality of transducer units associated with the object. Time delays are identified for a number of modes in the signals received at the plurality of transducer units. A determination is made as to whether a time delay in the time delays for the number of modes in the signals has a difference from a number of other time delays for the number of modes that is greater than a desired amount.

20 Claims, 16 Drawing Sheets

(56) References Cited

OTHER PUBLICATIONS

Thomas et al., "Corrosion Damage Detection with Piezoelectric Wafer Active Sensors", SPIE's 11th Annual International Symposium on Smart Structures and Materials and 9th Annual International Symposium on NDE for Health Monitoring and Diagnostics, Mar. 2004, San Diego CA, paper #5394-2, pp. 1-13.

Sohn et al., "Statistical Damage Classification under Changing environmental and Operational Conditions", Journal of Intelligent Materials Systems and Structures, 1992, pp. 1-17.

Oh et al., "Damage diagnosis under environmental and operational variations using unsupervised support vector machine", Elsevier, Journal of Sound and Vibration, 2009, pp. 1-16.

Park et al., "Time Reversal Active Sensing for Health Monitoring of a Composite Plate", Journal of Sound and Vibration, 2004, pp. 1-33.

Yeum et al., "Lamb wave mode decomposition using concentric ring and circular piezoelectric transducers", Wave Motion (2011), pp. 1-13.

Kim et al., "Instantaneous reference-free crack detection based on polarization characteristics of piezoelectric materials", Smart Materials and Structures, 2007, pp. 2375-2387.

Wooh et al., "Synthetic Phase Tuning of Guided Waves", IEEE Transactions on Ultrasonics, Ferroelectrics, and Frequency Control, vol. 48 No. 1, Jan. 2001, pp. 209-223.

Santoni et al., "Lamb Wave-Mode Tuning of Piezoelectric Wafer Active Sensors for Structural Health Monitoring", Transactions of the ASME, vol. 129, Dec. 2007, pp. 752-763.

U.S. Appl. No. 13/083,957, filed Apr. 11, 2011, Sohn et al.

Office Action, dated Aug. 22, 2012, regarding USPTO U.S. Appl. No. 13/083,957, 13 pages.

Notice of Allowance, dated May 30, 2013, regarding USPTO U.S. Appl. No. 13/083,957, 9 pages.

Final Office Action, dated Feb. 6, 2013, regarding USPTO U.S. Appl. No. 13/083,957, 10 pages.

\* cited by examiner

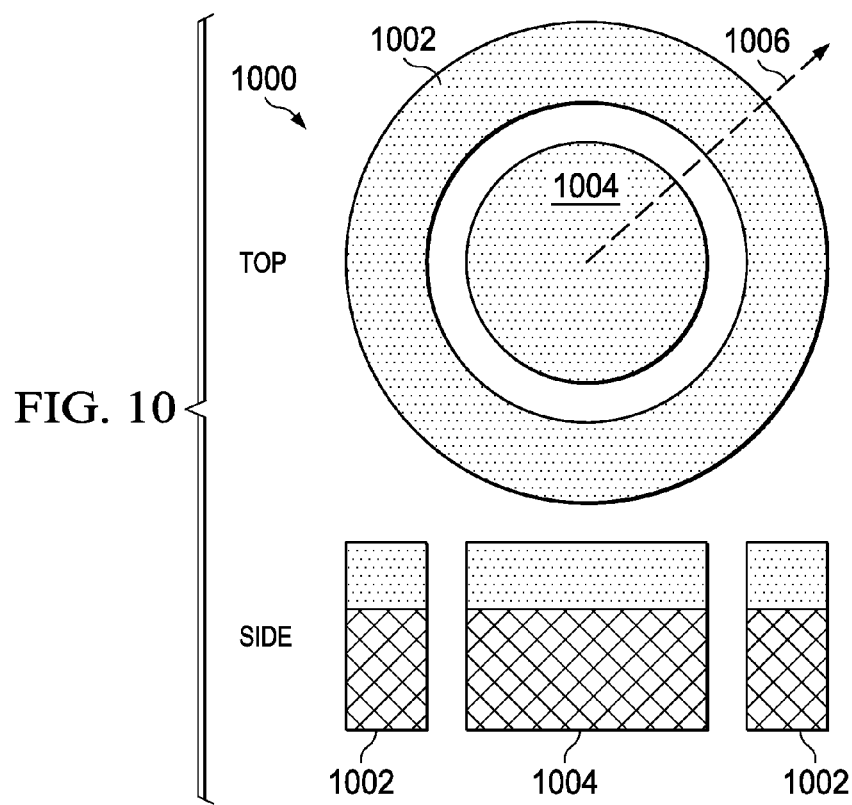
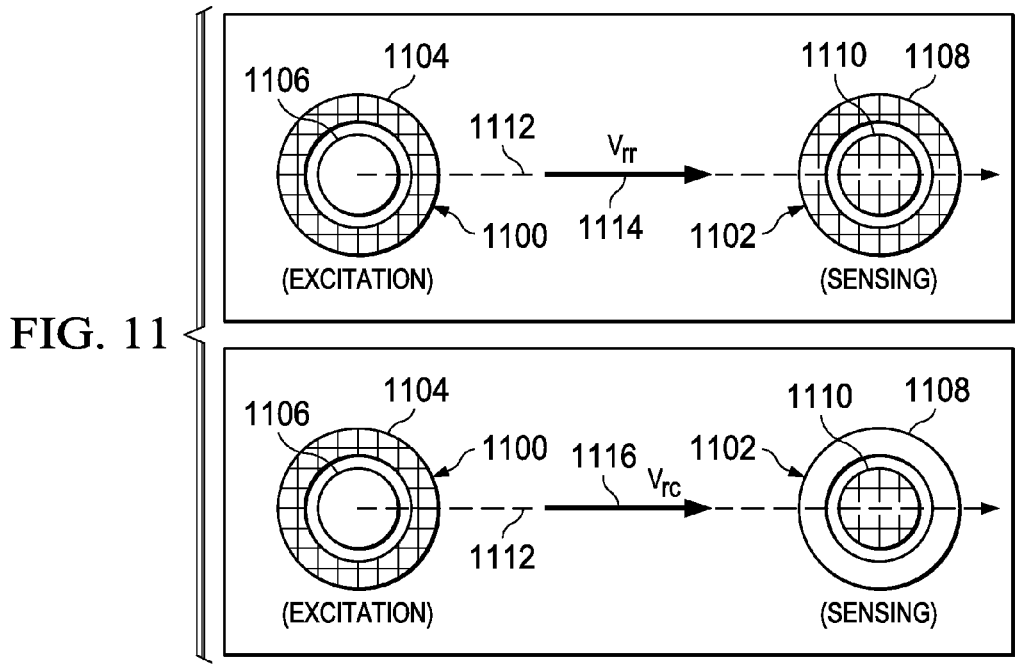

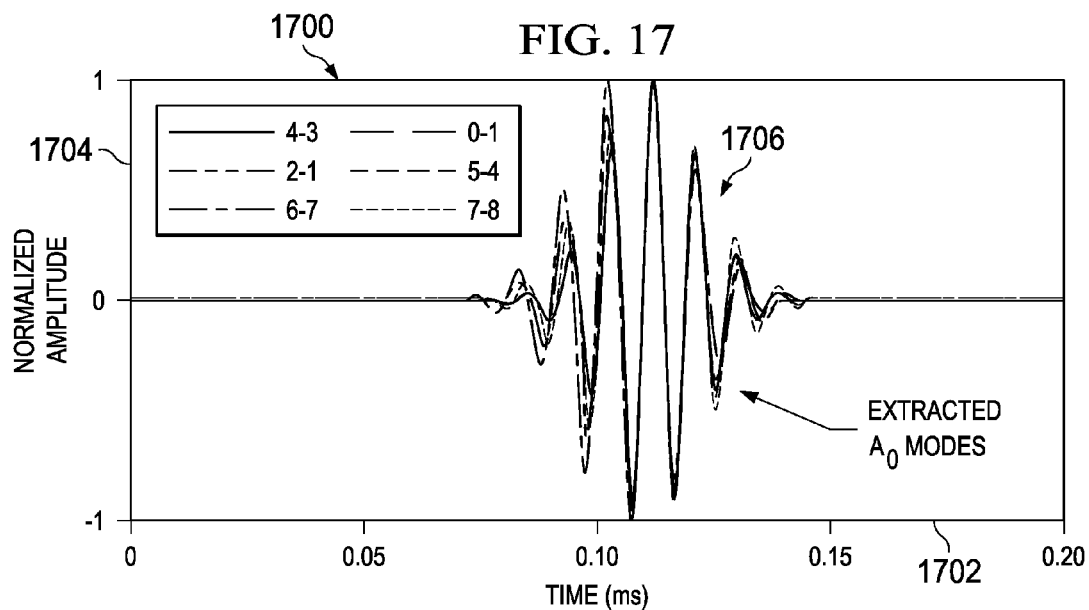
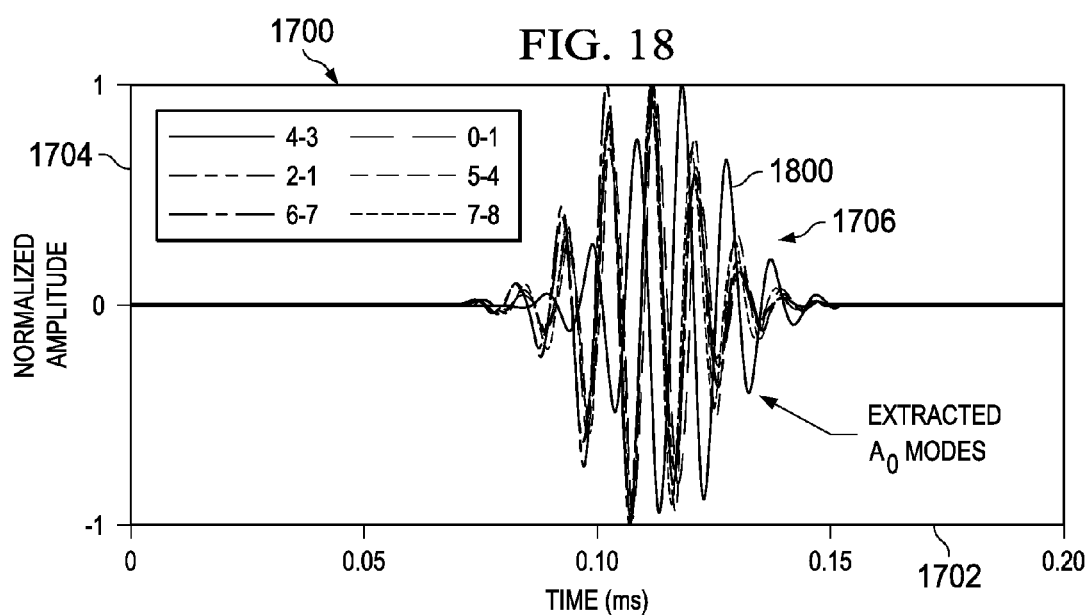

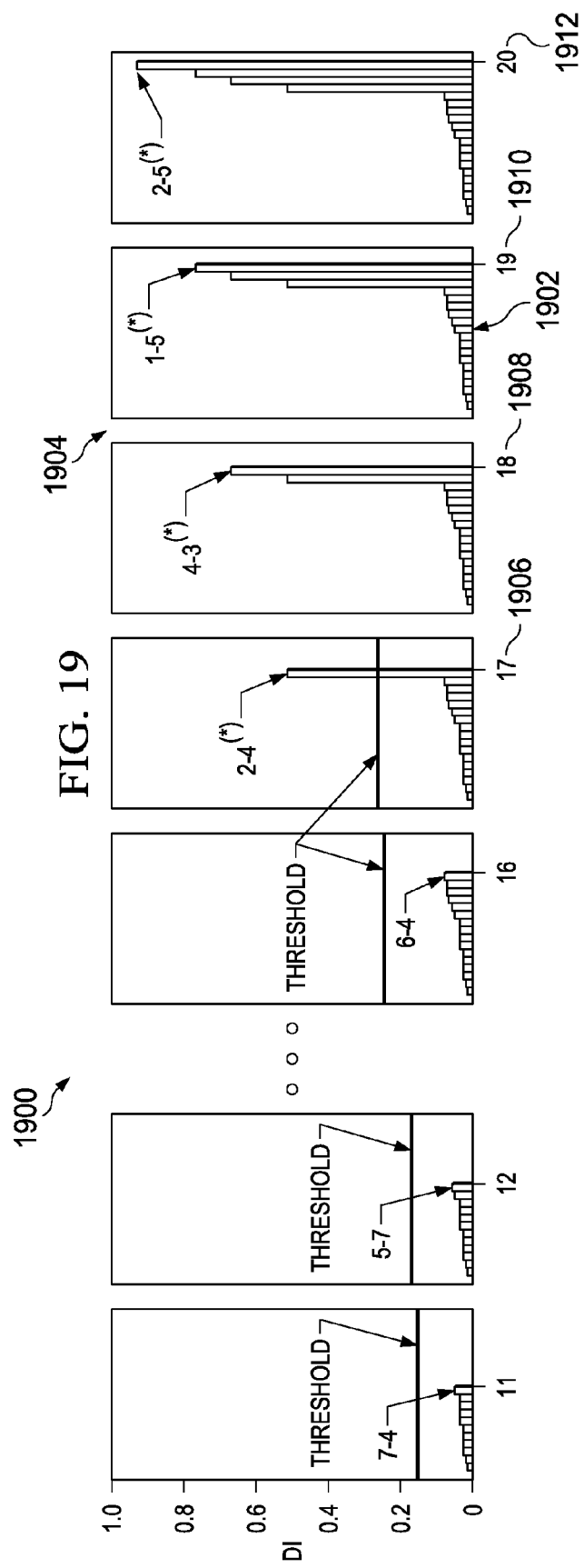

| CASE | DAMAGED LOCATION(S) 2010 | TEMPERATURE (°C) 2012 | THRESHOLD VALUE 2014 | DAMAGED PATH(S) (DI VALUE) 2016 |
|---|---|---|---|---|
| 1 | 0 (UNDAMAGE) | -10 | 0.164 | NONE |
|  |  | 20 | 0.247 | NONE |
|  |  | 50 | 0.276 | NONE |
| 2 | 1 (DAMAGE 1) | -10 | 0.176 | 4-3(0.674) |
|  |  | 20 | 0.262 | 4-3(0.842) |
|  |  | 50 | 0.285 | 4-3(0.702) |
| 3 | 2 (DAMAGES 1,2) | -10 | 0.189 | 4-3(0.693), 2-5(0.923) |
|  |  | 20 | 0.274 | 4-3(0.778), 2-5(0.875) |
|  |  | 50 | 0.266 | 4-3(0.725), 2-5(0.926) |
| 4 | 3 (DAMAGES 1,2,3) | -10 | 0.147 | 2-4(0.375), 4-3(0.647) 1-5(0.807), 2-5(0.921) |
|  |  | 20 | 0.279 | 2-4(0.339), 4-3(0.737) 1-5(0.841), 2-5(0.862) |
|  |  | 50 | 0.261 | 2-4(0.508), 4-3(0.663) 1-5(0.764), 2-5(0.930) |

FIG. 20

TIME DELAY BASED HEALTH MONITORING SYSTEM USING A SENSOR NETWORK

RELATED PROVISIONAL APPLICATION

This application is related to and claims the benefit of priority of provisional U.S. Patent Application Ser. No. 61/449,577, filed Mar. 4, 2011, entitled "Time Delay Based Health Monitoring System Using a Sensor Network", which is incorporated herein by reference.

CROSS-REFERENCE TO RELATED APPLICATION

This application is related to the following patent application entitled: "Transducer Based Health Monitoring System", Ser. No. 13/083,957; filed even date hereof, assigned to the same assignee, and incorporated herein by reference.

BACKGROUND INFORMATION

1. Field

The present disclosure relates generally to monitoring aircraft structures and, in particular, to monitoring aircraft structures for inconsistencies. Still more particularly, the present disclosure relates to a method and apparatus for detecting inconsistencies in aircraft structures using signals sent through the aircraft structures.

2. Background

Composite and metallic aircraft structures may be susceptible to internal changes that may occur from fatigue, impacts, and/or other events or conditions. Composite materials typically have a minimal visual indication of these types of changes. As a result, an aircraft may be inspected to assess the integrity of the structure on a periodic basis, or after visual indications of surface inconsistencies, such as a dent or a scratch.

For example, impacts to a structure, such as an aircraft, may occur during cargo loading and unloading. Inspections of the structure of an aircraft may be time consuming and costly in terms of the time and skill needed to perform the inspection. Further, an airline may incur a loss of revenue from the aircraft being out of service.

Structural health monitoring techniques have been developed and used to monitor materials and structures. These techniques often build the health monitoring systems into the structures. These health monitoring systems may be used to determine whether changes have occurred to these materials and structures over time.

Sudden changes in environments, such as electromagnetic effects, mechanical stresses, and other environmental effects may affect various materials and structures over time. By having health monitoring systems built into or associated with the structures to monitor the structures during use, appropriate measures and responses may be taken to prevent inconsistencies and may prolong the life span of these structures.

The monitoring of these structures may include various non-destructive elevation methods, such as ultrasonic testing or x-ray testing. Ultrasonic testing uses contact-based transducers to mechanically scan a structure. These sensors and actuators may be surface-mounted on the structure or may be embedded in the structure to generate and propagate signals into the structure being monitored.

A structural health monitoring system uses transducers to transmit waveforms at various frequency ranges and acquire data from the responses. Although structural health monitoring systems may provide an automated onboard system for detecting and characterizing inconsistencies or changes that may require maintenance, these types of systems may require updates and adjustments when maintenance, modifications, and reconfigurations of an aircraft occur.

For example, if a skin panel is changed, if a landing gear is modified, or if other changes occur, additional transducers may need to be moved or configured for use with the replaced or new components. These and other types of updates to the structural health monitoring system are time-consuming and expensive. The time needed to update the health monitoring system may make the aircraft unavailable for use longer than desired.

Therefore, it would be advantageous to have a method and apparatus that takes into account at least some of the issues discussed above, as well as possibly other issues.

SUMMARY

In one advantageous embodiment, a method for detecting an inconsistency in an object is provided. Signals sent on a plurality of paths in the object are received at a plurality of transducer units associated with the object. Time delays are identified for a number of modes in the signals received at the plurality of transducer units. A determination is made as to whether a time delay in the time delays for the number of modes in the signals has a difference from a number of other time delays for the number of modes that is greater than a desired amount.

In another advantageous embodiment, an apparatus comprises a signal analysis module. The signal analysis module is configured to identify time delays for a number of modes in signals received at a plurality of transducer units. The signals are received on a plurality of paths in an object in which the plurality of transducer units is associated with the object. The signal analysis module is configured to determine whether a time delay in the time delays for the number of modes in the signals has a difference from a number of other time delays in the time delays for the number of modes in the signals that is greater than a desired amount.

In yet another advantageous embodiment, a health monitoring system of an aircraft comprises a transducer system and a signal analysis module. The transducer system is associated with a number of structures in the aircraft. The signal analysis module is configured to cause a first plurality of transducer units associated with the number of structures in the aircraft to send signals on a plurality of paths in an object. The signal analysis module is configured to identify time delays for asymmetric modes in the signals received by a second plurality of transducer units in the transducer system. The signal analysis module is configured to determine whether a time delay in the time delays for the asymmetric modes in the signals has a difference from a number of other time delays for the asymmetric modes that is greater than a desired amount.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood with reference to the following detailed description of an advantageous embodiment of the present disclosure when read in conjunction with the accompanying drawings, wherein:

FIG. 10 is an illustration of a ring transducer unit in accordance with an advantageous embodiment;

FIG. 11 is an illustration of signals detected by two different segments of a transducer unit in accordance with an advantageous embodiment;

FIG. 17 is an illustration of a graph comparing extracted asymmetric modes for a group of paths in accordance with an advantageous embodiment;

FIG. 18 is an illustration of a graph comparing extracted asymmetric modes for a group of paths in accordance with an advantageous embodiment;

FIG. 19 is an illustration of a portion of the charts identifying index values for paths in accordance with an advantageous embodiment;

FIG. 20 is an illustration of a table containing the results of testing an object for inconsistencies under different conditions in accordance with an advantageous embodiment.

DETAILED DESCRIPTION

Figure 1:
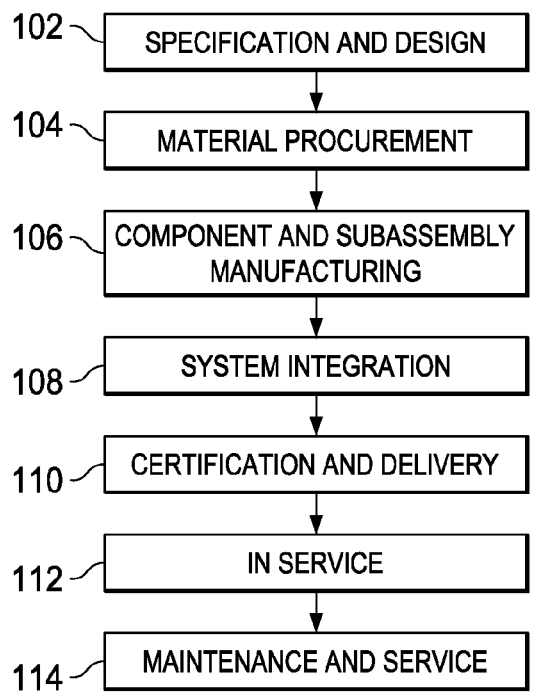
FIG. 1 is an illustration of an aircraft manufacturing and service method in accordance with an advantageous embodiment.
Figure 2:
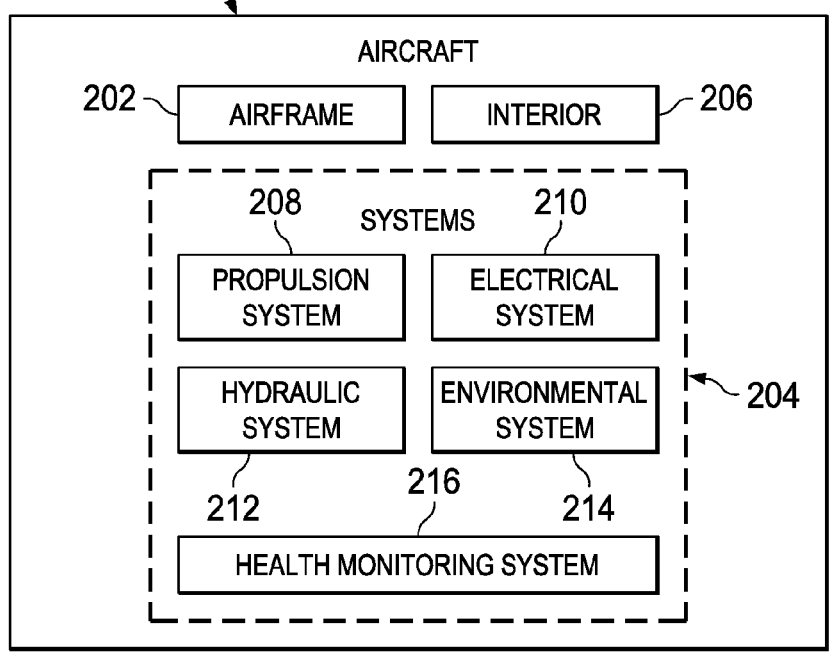
FIG. 2 is an illustration of an aircraft in which an advantageous embodiment may be implemented.

Referring more particularly to the drawings, advantageous embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service 112 by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed and/or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 2, an illustration of an aircraft is depicted in which an advantageous embodiment may be implemented. In this illustrative example, aircraft 200 is produced by aircraft manufacturing and service method 100 in FIG. 1 and may include airframe 202 with plurality of systems 204 and interior 206. Examples of plurality of systems 204 include one or more of propulsion system 208, electrical system 210, hydraulic system 212, environmental system 214, and health monitoring system 216. Any number of other systems may be included. Although an aerospace example is shown, different advantageous embodiments may be applied to other industries, such as the automotive industry.

Apparatuses and methods embodied herein may be employed during at least one of the stages of aircraft manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A or item A and item B. This example may also include item A, item B, and item C or item B and item C.

In one illustrative example, components or subassemblies produced in component and subassembly manufacturing 106 in FIG. 1 for health monitoring system 216 may be fabricated or manufactured in a manner similar to components or subassemblies produced for health monitoring system 216 while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A "number", when referring to items, means "one or more items." For example, a number of apparatus embodiments is one or more apparatus embodiments. A number of apparatus embodiments, method embodiments, or a combination thereof may be utilized while aircraft 200 is in service 112 and/or during maintenance and service 114 in FIG. 1. The use of a number of the different advantageous embodiments may substantially expedite the assembly of and/or reduce the cost of aircraft 200.

The different advantageous embodiments recognize and take into account a number of different considerations. For example, the different advantageous embodiments recognize and take into account that many currently used health monitoring systems that use baseline data may have a higher rate of false positive indications of inconsistencies than desired. These false indications may occur from different environmental and operational variations.

For example, the different advantageous embodiments recognize and take into account that many currently used health monitoring systems rely on baseline data. Baseline data is data generated from sending signals through structures in the aircraft during a time at which the structures are considered to have no inconsistencies.

The different advantageous embodiments recognize and take into account that this baseline data is typically generated under conditions that may vary from those present during operating conditions. For example, the data may be generated using the temperature, pressure, and other environmental factors that are present, while the aircraft or parts are on the ground or not installed. These parameters may change when the aircraft is operating. The parameters may also change between various phases of flight such as taxiing, takeoff, en route, landing, and other phases. Temperature, pressure, and other changes in the environment around an aircraft during operation of the aircraft may result in false indications of the presence of inconsistencies when compared to baseline data taken during generation of the baseline data when the aircraft is not in operation.

The different advantageous embodiments recognize and take into account that currently used health monitoring systems may attempt to compensate for changes in the environment. The different advantageous embodiments recognize and take into account that currently used systems may attempt to obtain data for the structures without inconsistencies under the different operating conditions that may occur to take into account changes that may occur in the environment. This information may then be used as a comparison to data generated during the operation of the aircraft to determine whether inconsistencies are present.

The different advantageous embodiments recognize and take into account, however, that this type of compensation for operating conditions may require recording more data than desired. The amount of data obtained for different environmental conditions may use more storage space than desirable in a health monitoring system. Further, the different advantageous embodiments also recognize and take into account that it may not be possible to record data from all possible types of operating conditions that may be encountered during the operation of the aircraft.

The different advantageous embodiments also recognize and take into account that this type of health monitoring system may also require re-recording of data when sensors are replaced. The different advantageous embodiments recognize and take into account that it would be desirable to detect inconsistencies without requiring the use of baseline data.

Thus, the different advantageous embodiments provide a method and apparatus for detecting inconsistencies in an object. In one advantageous embodiment, signals sent on a plurality of paths in the object are received at a plurality of transducer units associated with the object. Time delays are identified for a number of modes in the signals received at the plurality of transducer units. A determination is made as to whether a time delay in the time delays for the number of modes in the signals has a difference from a number of other time delays for the number of modes that is greater than a desired amount.

Figure 3:
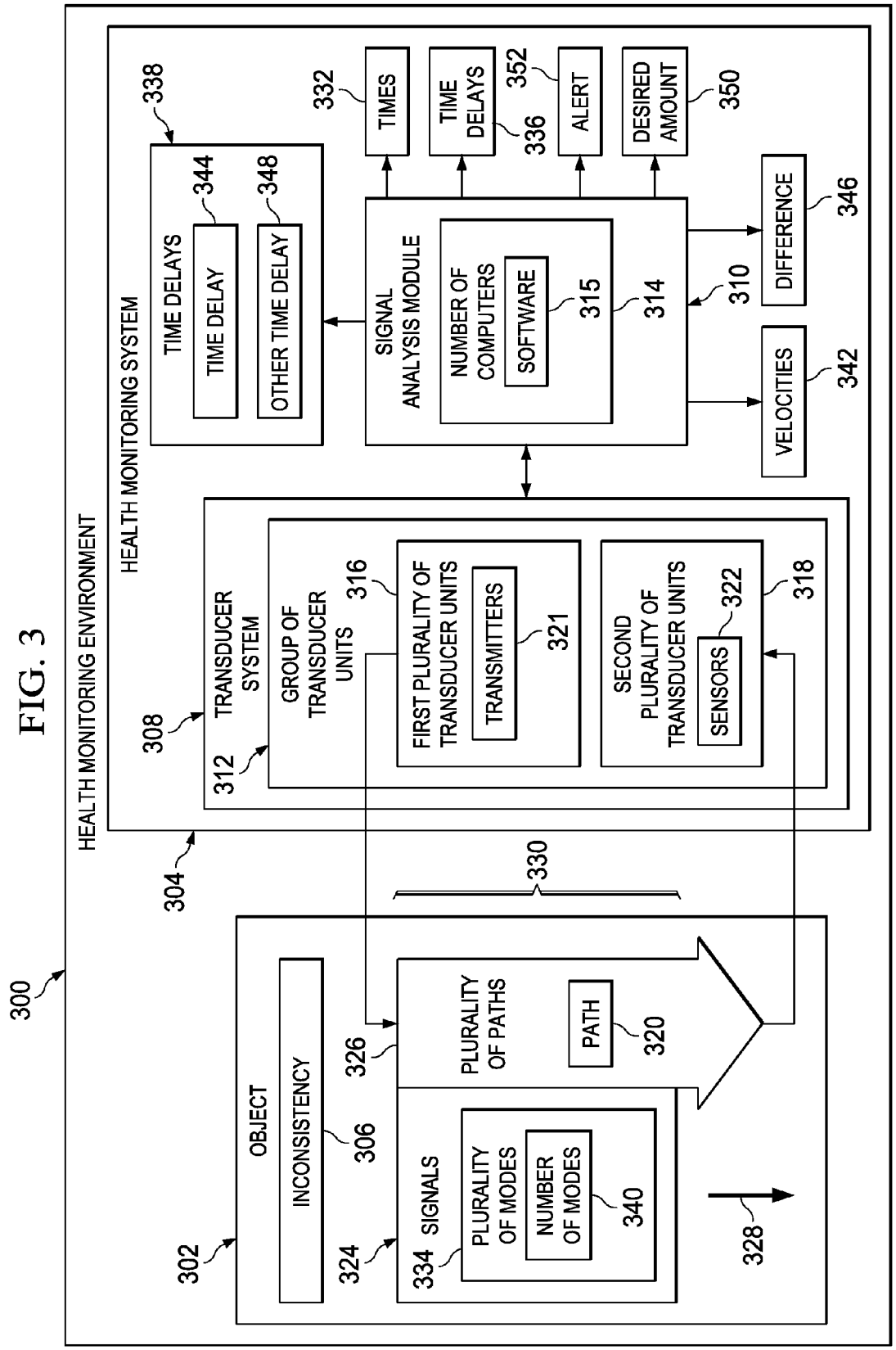
FIG. 3 is an illustration of a health monitoring environment in accordance with an advantageous embodiment.

With reference now to FIG. 3, an illustration of a health monitoring environment is depicted in accordance with an advantageous embodiment. Health monitoring environment 300 is an example of an environment that may be implemented in aircraft 200 in FIG. 2. As depicted, health monitoring environment 300 includes object 302 and health monitoring system 304 in this illustrative example.

In this illustrative example, object 302 is an example of an object that may be monitored using health monitoring system 304. In this illustrative example, object 302 may take various forms. In this example, object 302 takes the form of aircraft 200 or a structure or system within aircraft 200 in FIG. 2.

Health monitoring system 304 is associated with object 302. A first component may be considered to be associated with a second component by being secured to the second component, bonded to the second component, fastened to the second component, and/or connected to the second component in some other suitable manner. The first component may also be connected to the second component using a third component. The first component may also be considered to be associated with the second component by being formed as part of and/or an extension of the second component.

In these depicted examples, health monitoring system 304 is configured to detect a presence of inconsistency 306 in object 302. Inconsistency 306 may be any element or portion of object 302 that does not have a desired or expected state. Inconsistency 306 may be, for example, at least one of a delamination, a number of voids, and/or some other suitable type of inconsistency.

As depicted, health monitoring system 304 comprises transducer system 308 and signal analysis module 310. Transducer system 308 comprises group of transducer units 312. A transducer unit within group of transducer units 312 may function as a transmitter, a sensor, or both a transmitter and a sensor, depending on the particular implementation.

In these illustrative examples, group of transducer units 312 may be divided into first plurality of transducer units 316 and second plurality of transducer units 318. First plurality of transducer units 316 may be configured to function as transmitters 321. Second plurality of transducer units 318 may be configured to function as sensors 322.

Each transducer unit in group of transducer units 312 may include one or more transducers depending on the particular implementation. Transducers within group of transducer units 312 may be implemented using any known transducer configured to generate signals that may be sent through object 302. Additionally, transducers within group of transducer units 312 may also include transducers configured to receive signals 324 sent through object 302.

In these illustrative examples, transducer system 308 is connected to signal analysis module 310. Signal analysis module 310 is configured to control transducer system 308 in monitoring or testing object 302 for inconsistency 306.

In these illustrative examples, signal analysis module 310 is comprised of hardware, software, or a combination of the two. For example, signal analysis module 310 may be comprised of number of computers 314 with software 315.

Signal analysis module 310 is configured to cause first plurality of transducer units 316 to send signals 324 on plurality of paths 326. Signals 324 travel on path 320 to second plurality of transducer units 318 in these depicted examples. In these illustrative examples, plurality of paths 326 have same direction 328. Although plurality of paths 326 may have same direction 328, lengths 330 for paths within plurality of paths 326 may be different.

In particular, in these illustrative examples, plurality of paths 326 have same direction 328 when object 302 comprises composite materials. Composite materials, particularly in aircraft structures, generally have directionality of wave propagation. In other words, different wave speeds occur depending on the direction of the wave propagation.

For composite materials, when plurality of paths 326 do not have same direction 328, the arrival time of number of modes 340 may be unmated even if inconsistency 306 is not present in object 302. Of course, in other illustrative examples, plurality of paths 326 may have different directions.

Signals 324 travel from first plurality of transducer units 316 to second plurality of transducer units 318 in times 332. Times 332 are identified by signal analysis module 310. Times 332 may also be referred to as times of flight or times of travel.

Additionally, signals 324 have plurality of modes 334. In other words, each signal in signals 324 has plurality of modes 334. A mode, as used herein, is a component of a waveform that makes up a signal in signals 324. A mode is one type of physical propagation of waveforms in these illustrative examples.

In these illustrative examples, different modes within plurality of modes 334 for each signal of signals 324 may arrive at a sensor within second plurality of transducer units 318 at different times within times 332. These times are also referred to as time delays 336.

In these illustrative examples, signal analysis module 310 identifies time delays 338 for number of modes 340 in plurality of modes 334 for signals 324 received by second plurality of transducer units 318 in group of transducer units 312. In these illustrative examples, one mode is selected for number of modes 340. In other illustrative examples, additional modes may also be identified. Each time delay for a particular mode in number of modes 340 is identified for a particular path in plurality of paths 326.

Time delays 338 may be identified by signal analysis module 310 in the form of velocities 342. In other words, a velocity within velocities 342 is present for each mode in number of modes 340 for a particular path in plurality of paths 326. For example, a velocity is present in velocities 342 for each path in plurality of paths 326 for a particular mode in number of modes 340 along that path.

In these illustrative examples, time delays 338 may be measured using velocities 342. For example, when a signal in signals 324 is detected at second plurality of transducer units 318, signal analysis module 310 identifies the velocity for a mode in number of modes 340 for the signal at the time of detection. A slower velocity for the mode for the signal as compared to the velocities for the same mode in other signals in signals 324 may indicate that inconsistency 306 was encountered along the path in plurality of paths 326 for the signal. In this manner, a slower velocity for the signal indicates a time delay for the mode that may be caused by inconsistency 306. The velocity along with a length of the path may be used to calculate the time delay.

In this manner, lengths 330 for plurality of paths 326 may be different. As a result, normalizing for actual time in time delays 338 may be unnecessary when velocities 342 are used to represent time delays 338. A velocity within velocities 342 that varies from other velocities represents a difference in time delay as compared to the other velocities.

In these illustrative examples, signal analysis module 310 is configured to determine whether time delay 344 in time delays 338 has difference 346 from other time delays 348 in time delays 338 that is greater than desired amount 350. Time delay 344 is for a particular mode in number of modes 340 for a particular path associated with time delay 344. In other words, difference 346 may be greater than other time delays 348 and time delays 338 for number of modes 340 when inconsistency 306 is present along the path associated with time delay 344.

Signal analysis module 310 generates alert 352 if difference 346 of time delay 344 is greater than desired amount 350. Alert 352 is an indication that inconsistency 306 is present in object 302. In these illustrative examples, alert 352 may be a signal, a message, or some other suitable type of alert. Alert 352 may include other information. For example, alert 352 may include the particular path, the transmitting and receiving transducer, the time at which the inconsistency was detected, operating conditions, state of the aircraft, and other suitable information.

In some illustrative examples, time delays 338 for number of modes 340 may be identified without using velocities 342. For example, time delays 338 for number of modes 340 for signals 324 may be identified by normalizing lengths 330 for plurality of paths 326 along which signals 324 travel from first plurality of transducer units 316 to second plurality of transducer units 318. These normalized lengths may then be used to identify time delays 338.

Thus, the different advantageous embodiments in health monitoring environment 300 identify a presence of inconsistency 306 without needing or using baseline data.

The illustration of health monitoring environment 300 in FIG. 3 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, although object 302 has been described with respect to an aircraft, object 302 may take other forms. For example, object 302 may be selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, a building, a skin panel, an engine, a fuselage, a wing, a rib, and a stringer.

In yet other illustrative examples, additional signal analysis modules in addition to signal analysis module 310 may be present to provide for more coverage of object 302, redundancy, or for some other suitable purpose. Further, health monitoring system 304 may be embedded or built into object 302 in some illustrative examples. In other illustrative examples, health monitoring system 304 may be connected to or attached to object 302 for monitoring object 302 for a period of time and then removed or detached from object 302.

Additionally, although the different advantageous embodiments have been described for an object comprising composite materials, objects comprising other types of materials may also be tested using health monitoring system 304.

For example, object 302 may comprise materials such as, without limitation, steel, titanium, aluminum, a metal alloy, and/or other suitable types of materials. When object 302 is comprised of materials other than composite materials, paths in plurality of paths 326 may not all have same direction 328. In other words, paths in plurality of paths 326 may have different directions.

Figure 4:
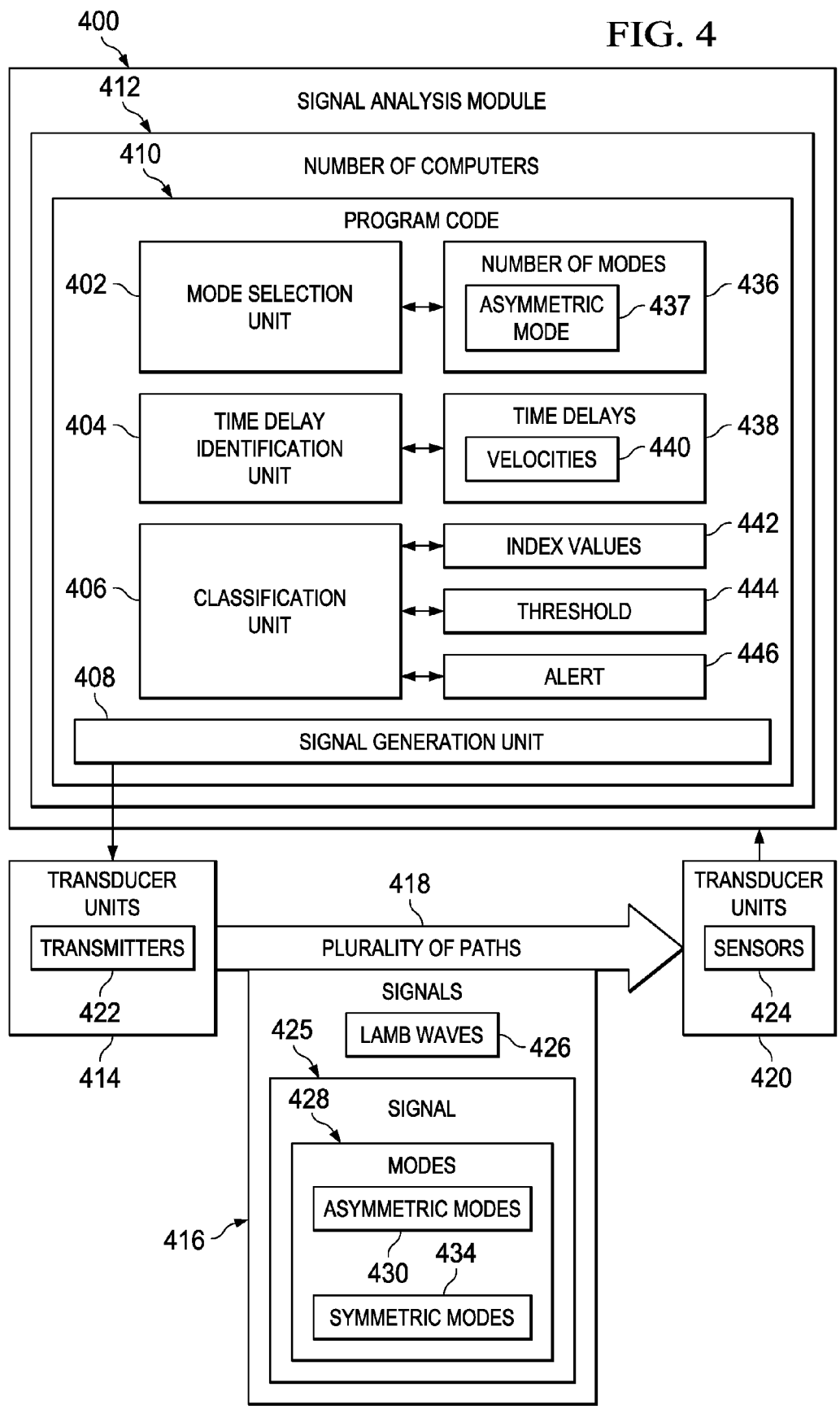
FIG. 4 is an illustration of a signal analysis module in accordance with an advantageous embodiment.

With reference now to FIG. 4, an illustration of a signal analysis module is depicted in accordance with an advantageous embodiment. Signal analysis module 400 is an example of one implementation for signal analysis module 310 in FIG. 3.

In this illustrative example, signal analysis module 400 includes mode selection unit 402, time delay identification unit 404, and classification unit 406. These different units may be implemented in hardware, software, or a combination of the two. As one illustrative example, these units may be implemented within program code 410 running on number of computers 412.

In this depicted example, signal generation unit 408 is configured to cause transducer units 414 to generate signals 416 that travel on plurality of paths 418 and are then detected by transducer units 420. Transducer units 414 function as transmitters 422, while transducer units 420 function as sensors 424.

In these illustrative examples, signals 416 take the form of Lamb waves 426. Lamb waves 426 are waves that propagate in solid media. For example, Lamb waves 426 may propagate within the thickness of an object, such as a plate, or other type of object. Signal 425 in signals 416 has modes 428. Modes 428 include asymmetric modes 430 and symmetric modes 434.

In these illustrative examples, asymmetric modes 430 may be affected more by certain types of inconsistencies in an object as compared to symmetric modes 434. In particular, asymmetric modes 430 may be affected more by inconsistencies in the form of delaminations as compared to symmetric modes 434.

In these illustrative examples, mode selection unit 402 identifies number of modes 436 in modes 428 for use in determining whether an inconsistency is present. In the depicted examples, number of modes 436 takes the form of asymmetric mode 437 in asymmetric modes 430. Of course, in other examples, additional asymmetric modes may be selected in addition to asymmetric mode 437 depending on the particular implementation.

With delamination of composite materials, an asymmetric mode in signals 416 is affected more than a symmetric mode in symmetric modes 434. Of course, for other types of materials, other modes may be selected in modes 428.

Number of modes 436 is selected as modes that may provide a greatest desired ability to identify inconsistencies in the object.

In these illustrative examples, this identification of number of modes 436 is performed for each signal in signals 416. After asymmetric mode 437 has been selected for signal 425 and the same asymmetric mode is selected for other signals in signals 416, time delays 438 in the form of velocities 440 are identified by time delay identification unit 404. In these illustrative examples, time delays 438 are used by classification unit 406 to generate index values 442. Index values 442 are used by classification unit 406 to determine whether an inconsistency is present along one of plurality of paths 418.

If any of index values 442 are greater than threshold 444, alert 446 is generated by classification unit 406 to indicate the presence of an inconsistency. In these illustrative examples, threshold 444 may be selected as a value that indicates that an inconsistency is present. An index value in index values 442 that is greater than threshold 444 may be considered an outlier. The selection of threshold 444 and index values 442 may be performed using various known statistical analysis techniques.

The illustration of signal analysis module 400 in FIG. 4 is not meant to imply physical or architectural limitations to the manner in which signal analysis module 310 in FIG. 3 may be implemented. In other illustrative examples, the different units may be implemented as a single unit, or other subdivisions may be made depending on the particular implementation.

Figure 5:
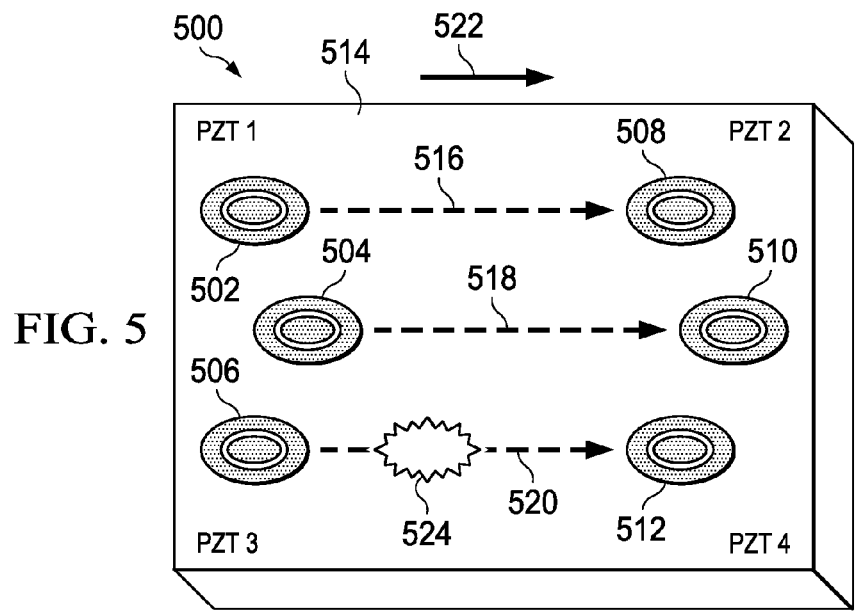
FIG. 5 is an illustration of a transducer system in accordance with an advantageous embodiment.

With reference now to FIG. 5, an illustration of a transducer system is depicted in accordance with an advantageous embodiment. In this illustrative example, transducer system 500 is an example of one implementation of transducer system 308 in FIG. 3. In this illustrative example, transducer units 502, 504, 506, 508, 510, and 512 are associated with skin panel 514. Skin panel 514 is a composite skin panel with composite layers in these illustrative examples. Skin panel 514 is an example of one implementation for object 302 or a portion of object 302 in FIG. 3.

As depicted, transducer units 502, 504, and 506 function as transmitters, while transducer units 508, 510, and 512 function as sensors. In these illustrative examples, transducer unit 502 and transducer unit 508 form path 516, transducer unit 504 and transducer unit 510 form path 518, and transducer unit 506 and transducer unit 512 form path 520. As can be seen in these illustrative examples, path 516, path 518, and path 520 extend in the direction of arrow 522. All of these paths have the same direction.

Although the paths are illustrated as having the same length, these paths may have different lengths depending on the particular implementation. Also, in other tests, transducer units 502, 504, and 506 may become sensors while transducer units 508, 510, and 512 become transmitters. In this case, the paths formed between the transducer units have a direction that is in the opposite direction of arrow 522. Of course, paths may be generated by other combinations of transducer units in these examples, having the same direction.

In this illustrative example, inconsistency 524 is present along path 520. Inconsistency 524 takes the form of a delamination of layers within skin panel 514.

Inconsistency 524 results in a time delay for signals sent along path 520 being greater than those sent along paths 516 and 518. As a result, the velocity of a signal sent along path 520 will be less than the velocities of signals sent along paths 516 and 518. This difference in velocities is used to identify the presence of inconsistency 524.

Figure 6:
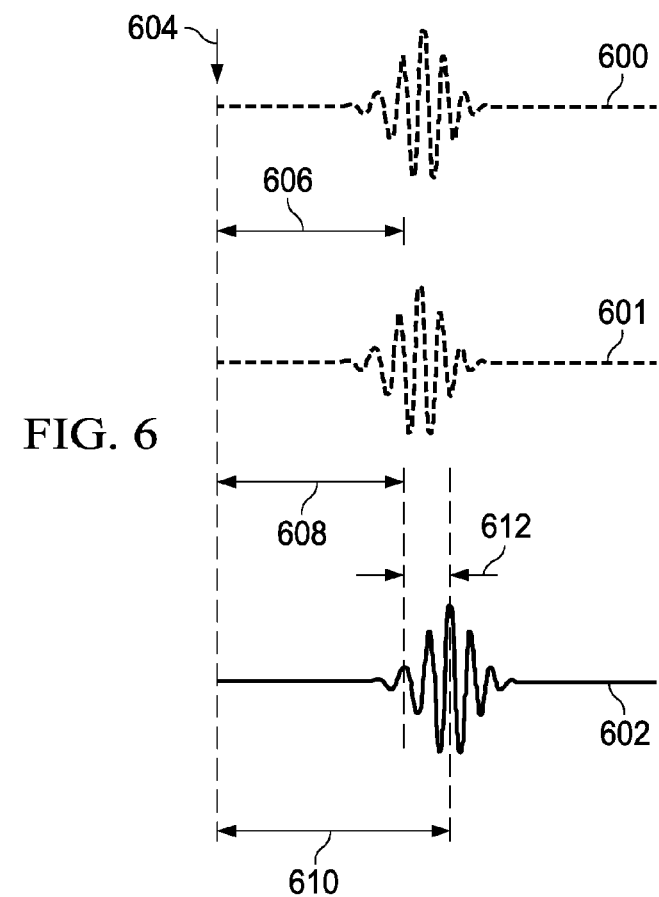
FIG. 6 is an illustration of graphs identifying a time delay for a signal due to a presence of an inconsistency in accordance with an advantageous embodiment.

With reference now to FIG. 6, an illustration of graphs identifying a time delay for a signal due to a presence of an inconsistency is depicted in accordance with an advantageous embodiment. Asymmetric mode waveforms 600, 601, and 602 may be waveforms extracted from signals transmitted and received by transducer units.

In this illustrative example, asymmetric mode waveform 600 is the asymmetric mode extracted from a signal transmitted by transducer unit 502 along path 516 in FIG. 5. Asymmetric mode waveform 601 is the asymmetric mode extracted from a signal transmitted by transducer unit 504 along path 518 in FIG. 5. Asymmetric mode waveform 602 is the asymmetric mode extracted from a signal transmitted by transducer unit 506 along path 520 in FIG. 5.

As illustrated, asymmetric mode waveforms 600, 601, and 602 are transmitted at substantially the same time. In particular, asymmetric mode waveforms 600, 601, and 602 are transmitted at initial transmission time 604 in this example.

Time 606 is the time it takes for asymmetric mode waveform 600 to reach transducer unit 508 along path 516 in FIG. 5. Time 608 is the time it takes for asymmetric mode waveform 601 to reach transducer unit 510 along path 518 in FIG. 5. Time 610 is the time it takes for asymmetric mode waveform 602 to reach transducer unit 512 along path 520 in FIG. 5. Times 606, 608, and 610 may also be referred to as times of flight for asymmetric mode waveforms 600, 601, and 602, respectively.

Time delay 612 is the difference between time 610 and time 608. Time delay 612 is the same difference between time 610 and time 606. With paths 516, 518, and 520 having substantially the same length, the presence of time delay 612 indicates that inconsistency 524 is present along path 520. In other words, when one of times 606, 608, and 610 is not substantially the same as the other times, an inconsistency is present along the corresponding path in skin panel 514. When times 606, 608, and 610 are substantially the same, an inconsistency is not present along the corresponding paths.

In this manner, the identification of inconsistencies does not require the use of prior baseline data. Further, this process may be performed to identify inconsistencies even under changing operational and environmental conditions of the object.

Figure 7:
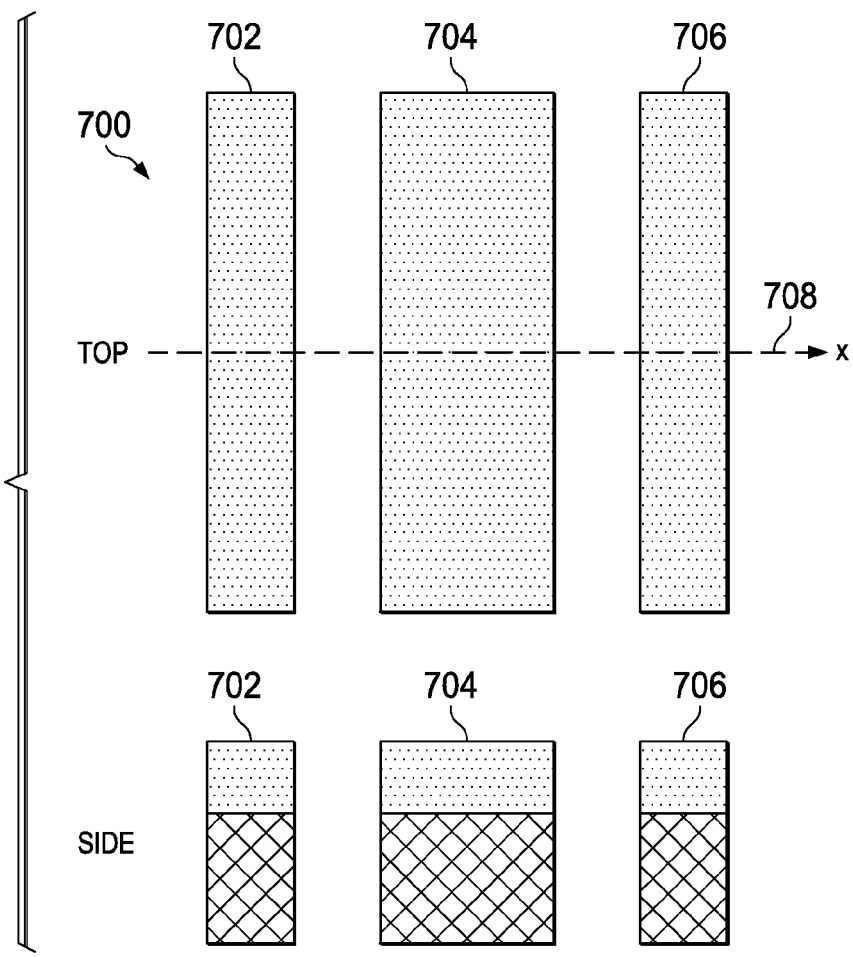
FIG. 7 is an illustration of three transducers for a transducer unit in accordance with an advantageous embodiment.

With reference now to FIGS. 7-10, examples of transducer units are depicted in accordance with an advantageous embodiment. In FIG. 7, an illustration of three transducers for a transducer unit is depicted in accordance with an advantageous embodiment. In this illustrative example, transducer unit 700 is shown in a top view and a side view. Transducer unit 700 comprises transducer 702, 704, and 706. As can be seen, transducer unit 700 is symmetric along axis 708.

Figure 8:
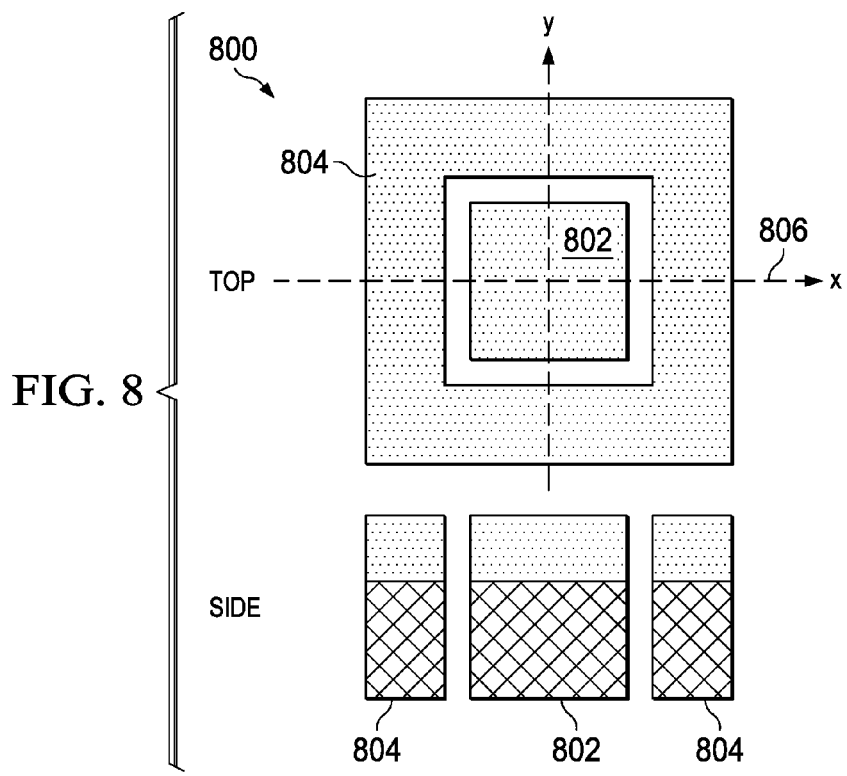
FIG. 8 is a two-segment transducer unit in accordance with an advantageous embodiment.

In FIG. 8, an illustration of a two-segment transducer unit is depicted in accordance with an advantageous embodiment. In this illustrative example, transducer unit 800 comprises segment 802 and segment 804. Transducer unit 800 is symmetric about axis 806.

Figure 9:
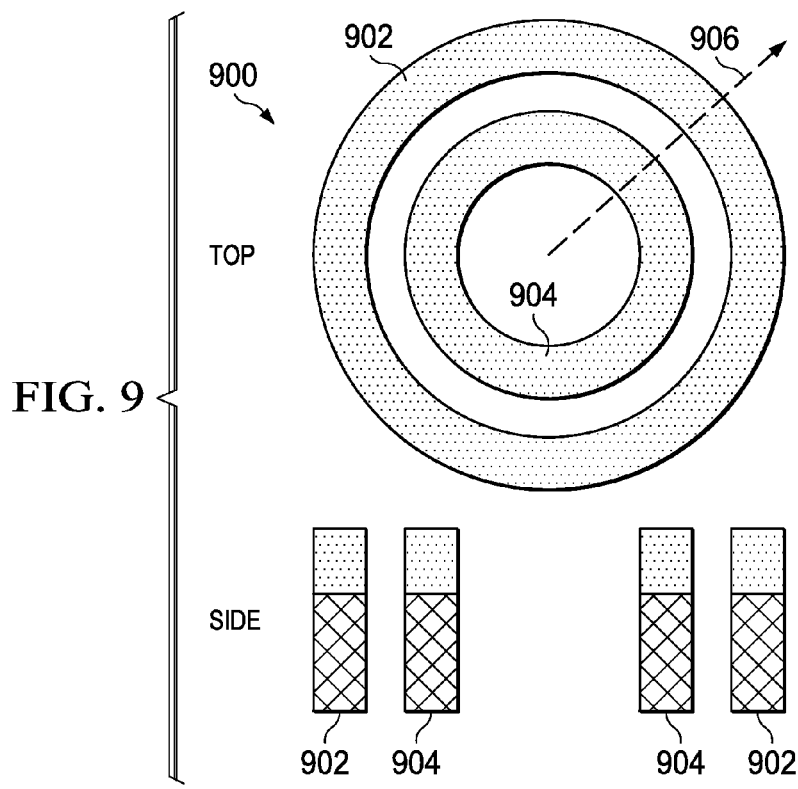
FIG. 9 is an illustration of a ring-based transducer in accordance with an advantageous embodiment.

With reference now to FIG. 9, an illustration of a ring-based transducer is depicted in accordance with an advantageous embodiment. In this illustrative example, transducer unit 900 comprises segment 902 and segment 904. Segment 902 is a ring segment. Segment 904 is a circular segment. Transducer unit 900 is symmetric about axis 906 in these examples.

With reference now to FIG. 10, an illustration of a ring transducer unit is depicted in accordance with an advantageous embodiment. In this illustrative example, transducer unit 1000 comprises segment 1002 and segment 1004. Segment 1002 is a ring segment. Segment 1004 is a circular segment. Transducer unit 1000 is symmetric about axis 1006 in these illustrative examples.

With reference now to FIG. 11, an illustration of signals detected by two different segments of a transducer unit is depicted in accordance with an advantageous embodiment. In this illustrative example, transducer unit 1100 functions as a transmitter, while transducer unit 1102 functions as a sensor. Transducer unit 1100 has ring segment 1104 and circular segment 1106, while transducer unit 1102 has ring segment 1108 and circular segment 1110.

As depicted in this illustrative example, path 1112 is formed between transducer unit 1100 and transducer unit 1102. Activation of different segments for the transducer units allows four different Lamb wave signals to be obtained.

For example, when ring segment 1104 of transducer unit 1100 is activated, signal 1114, $V_{rr}$, is detected by ring segment 1108 of transducer unit 1102. Further, when ring segment 1104 is activated, signal 1116, $V_{rc}$, is detected by circular segment 1110 of transducer unit 1102. Two different Lamb wave signals (not shown), $V_{cr}$ and $V_{cc}$, may be obtained when circular segment 1106 of transducer unit 1100 is activated.

In this illustrative example, the modes for signal 1114 and signal 1116 may have substantially identical arrival times at ring segment 1108 and circular segment 1110, respectively, but different amplitudes. Further, the amplitudes of the symmetric ($S_0$) modes and the asymmetric ($A_0$) modes change at different rates as the size of the segment in the transmitting transducer unit that transmits the signal and the size of the segment in the sensing transducer unit that detects the signal changes.

In other words, the amplitudes of the symmetric modes and the asymmetric modes change depending on which segment is activated to transmit in transducer unit 1100 and which segment is activated to detect in transducer unit 1102.

Additionally, the rate at which the amplitude of each mode in the modes for the signal changes, with respect to the size of the particular segments in the transducer units, is not based on the distance between transducer unit 1100 and transducer unit 1102.

Signal 1114 and signal 1116 may be used by, for example, signal analysis module 400 in FIG. 4 to identify a number of modes for which time delays may be identified. For example, signal 1114 and signal 1116 may be measured at ring segment 1108 and circular segment 1110 for transducer unit 1102. The amplitudes of the symmetric modes in signal 1114 and signal 1116 are normalized such that the amplitudes of the symmetric modes are substantially equal.

The symmetric modes may then be removed by subtracting signal 1114, $V_{rr}$, from signal 1116, $V_{rc}$. In other words, the symmetric modes are subtracted from each other such that only the asymmetric mode remains. The asymmetric mode waveform formed by this subtraction does not preserve amplitude information. However, this signal does retain arrival time information for the asymmetric mode. In this manner, time delay information may be identified using the asymmetric mode waveform.

However, the asymmetric mode waveform contains information for the time of travel between transducer unit 1100 and transducer unit 1102. In this manner, time delay information may be identified using the asymmetric mode waveform.

Figure 12:
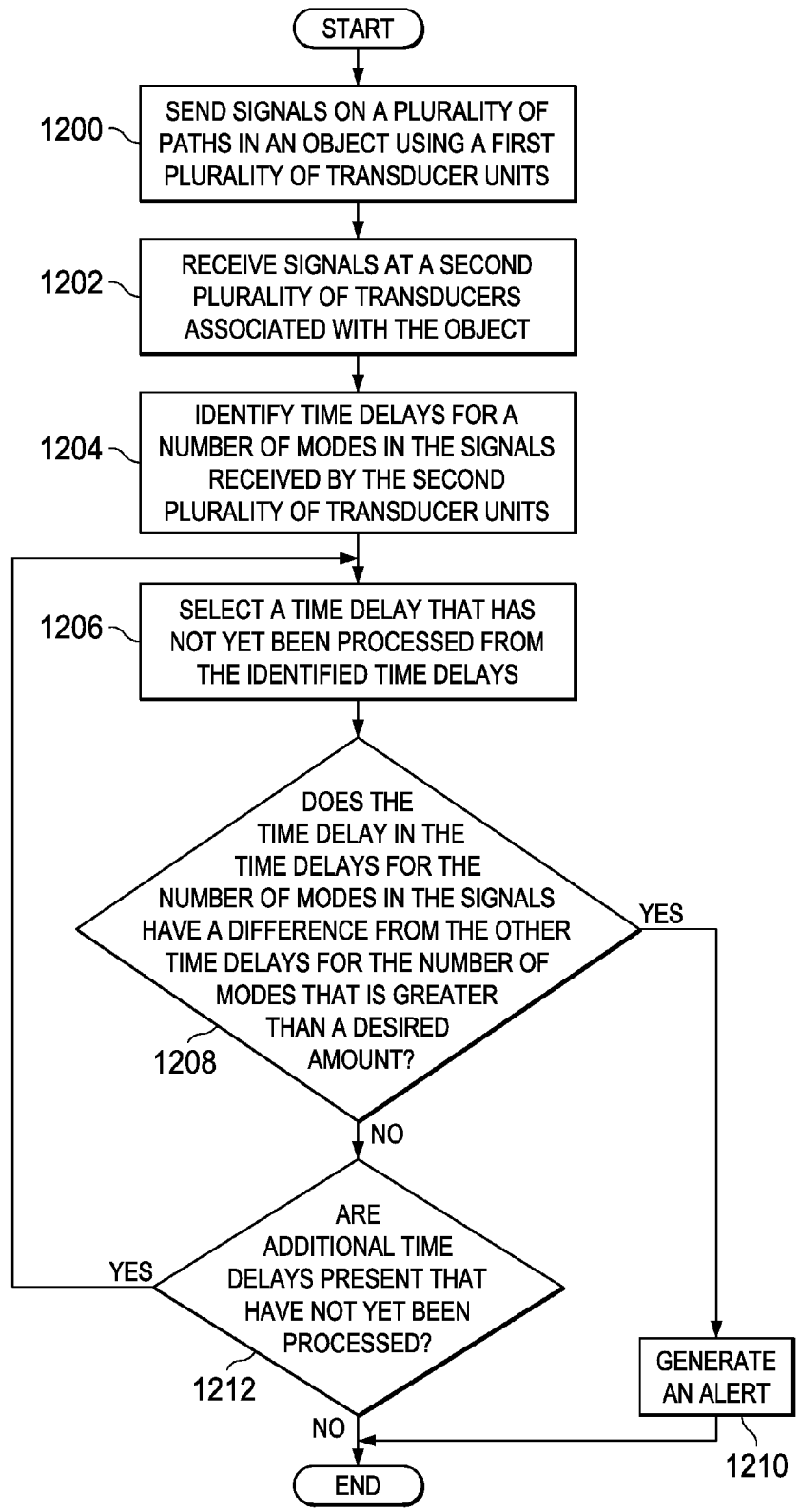
FIG. 12 is an illustration of a flowchart of a process for detecting an inconsistency in an object in accordance with an advantageous embodiment.

With reference now to FIG. 12, an illustration of a flowchart of a process for detecting an inconsistency in an object is depicted in accordance with an advantageous embodiment. The process illustrated in FIG. 12 may be implemented in health monitoring environment 300 in FIG. 3. In particular, this process may be implemented within signal analysis module 310 in FIG. 3.

The process begins by sending signals on a plurality of paths in an object using a first plurality of transducer units (operation 1200). This first plurality of transducer units functions as transmitters. Signals are received at a second plurality of transducers associated with the object (operation 1202). The second plurality of transducer units functions as sensors.

The process then identifies time delays for a number of modes in the signals received by the second plurality of transducer units (operation 1204). In this illustrative example, the number of modes includes one type of mode. The process then selects a time delay that has not yet been processed from the identified time delays (operation 1206). A determination is then made as to whether a time delay in the time delays for the number of modes in the signals has a difference from the other time delays for the number of modes that is greater than a desired amount (operation 1208).

If the time delay for the number of modes has a difference from the other time delays for the number of modes that is greater than the desired amount, the process generates an alert (operation 1210) and terminates thereafter.

With reference again to operation 1208, if the time delay for the number of modes has a difference from the other time delays for the number of modes that is not greater than the desired amount, a determination is made as to whether additional time delays are present that have not yet been processed (operation 1212). If additional time delays are not present, the process terminates. Otherwise, the process returns to operation 1206 to select another time delay that has not yet been processed from the identified time delays.

Figure 13:
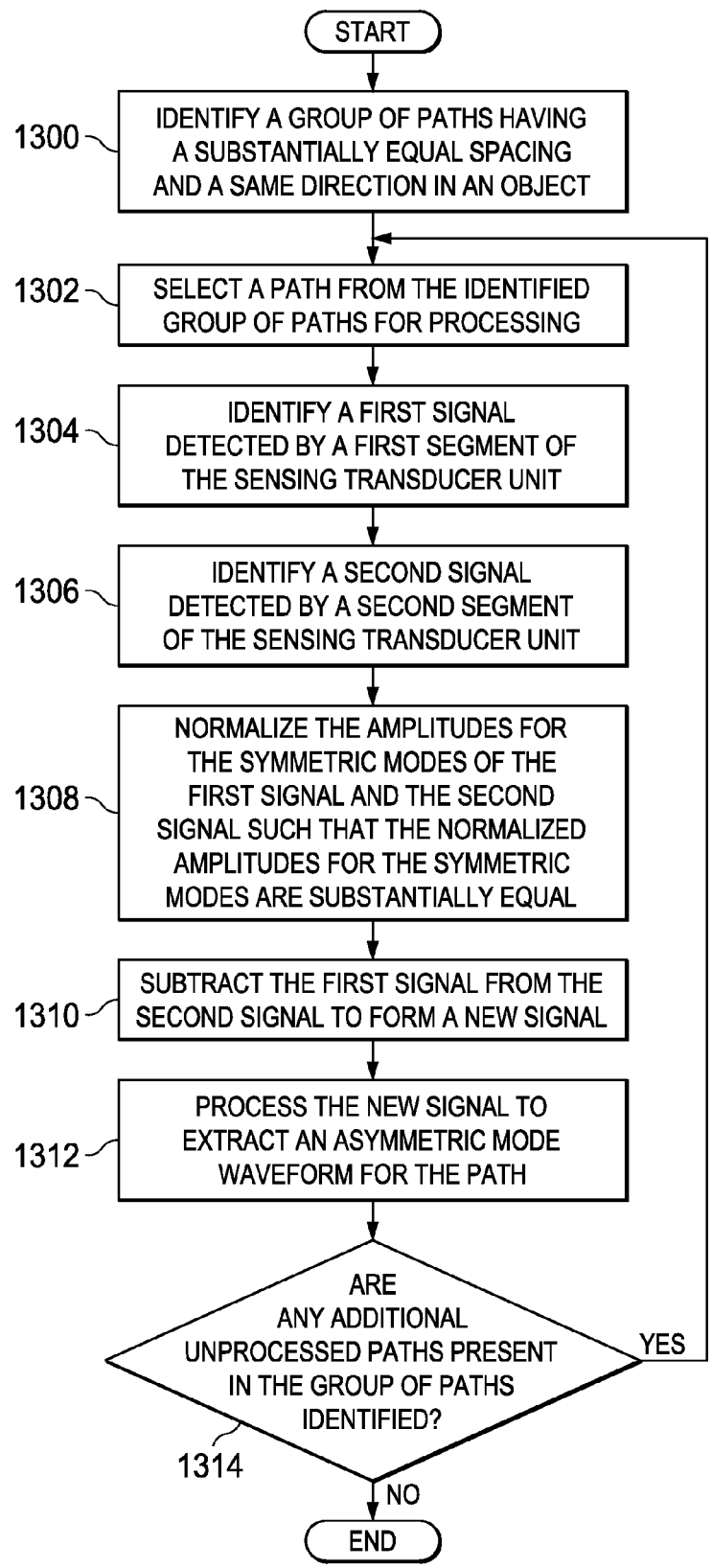
FIG. 13 is a flowchart of a process for selecting modes in signals received at transducers in accordance with an advantageous embodiment.

With reference now to FIG. 13, a flowchart of a process for selecting modes in signals received at transducers is depicted in accordance with an advantageous embodiment. The process illustrated in FIG. 13 may be implemented in signal analysis module 400 and, in particular, within mode selection unit 402 in signal analysis module 400 in FIG. 4.

The process begins by identifying a group of paths having a substantially equal spacing and a same direction in an object (operation 1300). In operation 1300, the object may be, for example, a composite skin panel. The object may have a number of inconsistencies in the object.

The paths are formed by transducer units placed on or in the object. In particular, the paths are formed along the distances between pairs of transducer units. For example, a signal transmitted by a transducer unit functioning as a transmitter travels along a path to a transducer unit functioning as a sensor. The transducer unit functioning as the sensor detects and measures the signal.

In this illustrative example, the transducer units may be any of a number of different forms having a number of segments. In one illustrative example, the transducer units take the form of, for example, transducer unit 800 in FIG. 8, transducer unit 900 in FIG. 9, transducer unit 1100 in FIG. 11, and/or transducer unit 1102 in FIG. 11. In other words, each of the transducer units forming the paths identified may have a ring segment and a circular segment. Of course, in other illustrative examples, other types of transducer units having segments with other types of shapes may be used.

The process selects a path from the identified group of paths for processing (operation 1302). The process then identifies a first signal detected by a first segment of the sensing transducer unit (operation 1304). The first segment may be a ring segment. The process identifies a second signal detected by a second segment of the sensing transducer unit (operation 1306). The second segment may be a circular segment. In this illustrative example, the first signal and the second signal may be detected by the first segment and the second segment, respectively, at substantially the same time.

Thereafter, the process normalizes the amplitudes for the symmetric modes of the first signal and the second signal such that the normalized amplitudes for the symmetric modes are substantially equal (operation 1308). The process then subtracts the first signal from the second signal to form a new signal (operation 1310).

Next, the new signal is processed to extract an asymmetric mode waveform for the path (operation 1312). The asymmetric mode waveform contains information about the amount of time the first signal and the second signal take traveling along the path from the transmitting transducer unit to the sensing transducer unit.

The process then determines whether any additional unprocessed paths are present in the group of paths identified (operation 1314). If additional unprocessed paths are not present, the process terminates. Otherwise, the process returns to operation 1302 as described above.

The process illustrated in FIG. 13 may be performed for each group of paths that are substantially equally spaced and have a same direction.

Figure 14:
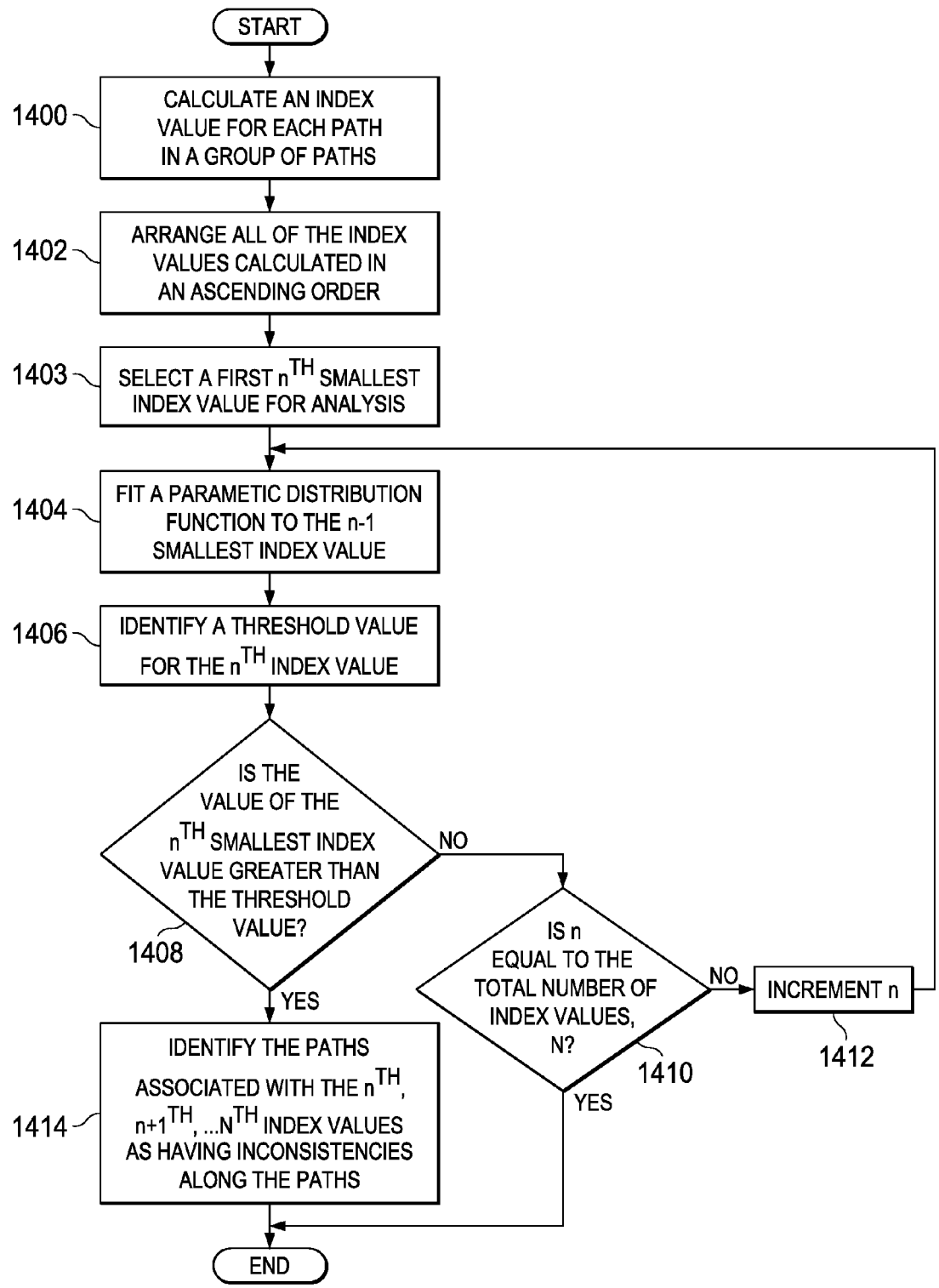
FIG. 14 is an illustration of a classification process for paths in accordance with an advantageous embodiment.

With reference now to FIG. 14, an illustration of a classification process for paths is depicted in accordance with an advantageous embodiment. The process illustrated in FIG. 14 may be implemented in classification unit 406 in signal analysis module 400 in FIG. 4. Further, this process may be implemented after the process illustrated in FIG. 13.

The process begins by calculating an index value for each path in a group of paths (operation 1400). In operation 1400, the group of paths is the group of paths identified in operation 1300 in FIG. 13.

The index value is calculated to identify the time delay for the asymmetric mode identified for each path. The index value is calculated based on an assumption that more than half of the paths in the group of paths are along portions of the object without inconsistencies.

The index value may be calculated using the following equations:

$$DI(i, \Omega) = \frac{1}{2}\left(1 - \frac{2}{n_d}\sum_{j}^{n_d/2} \text{corr}(A_0(i, \Omega), A_0(j, \Omega))\right)$$

$$DI(i) = \frac{1}{N}\sum_{\Omega}^{N} DI(I, \Omega).$$

where DI is the index value, i is an identifier for a particular path, $\Omega$ is an input frequency, d is an identifier for the group of paths, $n_d$ is the number of paths in a group of paths, corr is the cross-correlation function, j is the identifier for a path along which an inconsistency is not present, $A_0$ is the asymmetric mode, and $A_0(i, \Omega)$ and $A_0(j, \Omega)$ are the first arrival asymmetric modes at the input frequency $\Omega$ in the i and j paths, respectively. The j paths are selected as the half of the asymmetrical modes that are the fastest asymmetrical modes in the group of paths d.

In these illustrative examples, the first arrival asymmetric mode or the first arrival $A_0$ mode is a first asymmetric mode that arrives at the sensor. For example, the signals received at a sensor often include multiple modes. These modes may be, for example, directly propagated waves from a transmitter and a sensor, reflections from the structural boundary of the object, and/or from other types of sources. If an inconsistency is present between the sensor and the transmitter, only the first arrival $A_0$ mode is affected.

The index value DI indicates how much a signal traveling along a particular path is delayed as compared with other paths along which inconsistencies are not present.

The index value DI is normalized to have a range between 0 and 1 by subtracting the cross-correlation values from one and dividing it by 2. If the asymmetric mode obtained for a particular path has a similar arrival time with the asymmetric modes obtained for other paths along which inconsistencies are assumed to not be present, the index value approaches 0. Otherwise, if the asymmetric mode is delayed, the corresponding index value approaches 1.

Thereafter, the process arranges all of the index values calculated in an ascending order (operation 1402). In the ascending order, the first index value is the smallest index value and the $N^{th}$ index value is the largest index value. The $N^{th}$ index value is the last index value. In this illustrative example, N is the total number of index values. Further, each index value is for a particular path. In this manner, N is the total number of paths.

Next, the process selects a first $n^{th}$ smallest index value for analysis (operation 1403). In this example, n is an identifier for a particular index value in the group of index values. In operation 1403, the first index value may be selected as about half of the total number of paths. For example, if 20 paths are in the group of paths, the first n is selected as 10. In this manner, the $10^{th}$ smallest index value is selected as the first index value for analysis.

The process then fits a parametric distribution function to the n−1 smallest index value (operation 1404). For example, in operation 1404, when the 10$^{th}$ index value is selected, a parametric distribution function is fitted to the nine smallest index values in the group of index values.

A truncated exponential distribution is used for the parametric distribution function in this illustrative example. This distribution is bounded because the index values have the upper limit of 1 and the lower limit of 0. A truncated exponential distribution with parameter c has the following probability density function:

$$f(x) = ce^{-cx}(1-e^{-c})^{-1}, (0 < x \leq 1).$$

where f(x) is the probability density function, e is the exponential function, and x is the index value. Further, the maximum likelihood estimator of c is denoted as $c_b$. The maximum likelihood estimator $c_b$ can estimate a parameter of c of the best-fit truncated exponential distribution of x as follows:

$$\bar{x} = 1/c_b - 1/(e^{c_b} - 1).$$

where $$\bar{x}$$

is the mean of x.

The process then identifies a threshold value for the n$^{th}$ index value (operation 1406). In operation 1406, the threshold value is identified based on fitting the parametric distribution function to the n−1 smallest index values in operation 1404 and a specific confidence level. This confidence level may be set by user input.

Next, the process determines whether the value of the n$^{th}$ smallest index value is greater than the threshold value (operation 1408). If the value of the n$^{th}$ smallest index value is not greater than the threshold value, the process determines whether n is equal to the total number of index values, N (operation 1410). If n is not equal to the total number of index values, N, the process increments n (operation 1412). Then the process returns to operation 1404 as described above.

With reference again to operation 1410, if n is equal to the total number of index values, N, the process terminates. Further, with reference again to operation 1408, if the value of the n$^{th}$ smallest index value is greater than the threshold value, the process identifies the paths associated with the n$^{th}$, n+1$^{th}$, ... N$^{th}$ index values as having inconsistencies along the paths (operation 1414), with the process terminating thereafter.

The flowcharts and block diagrams in the different depicted embodiments illustrate the architecture, functionality, and operation of some possible implementations of apparatus and methods in different advantageous embodiments. In this regard, each block in the flowchart or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved. Also, other blocks may be added in addition to the illustrated blocks in a flowchart or block diagram.

Figure 15:
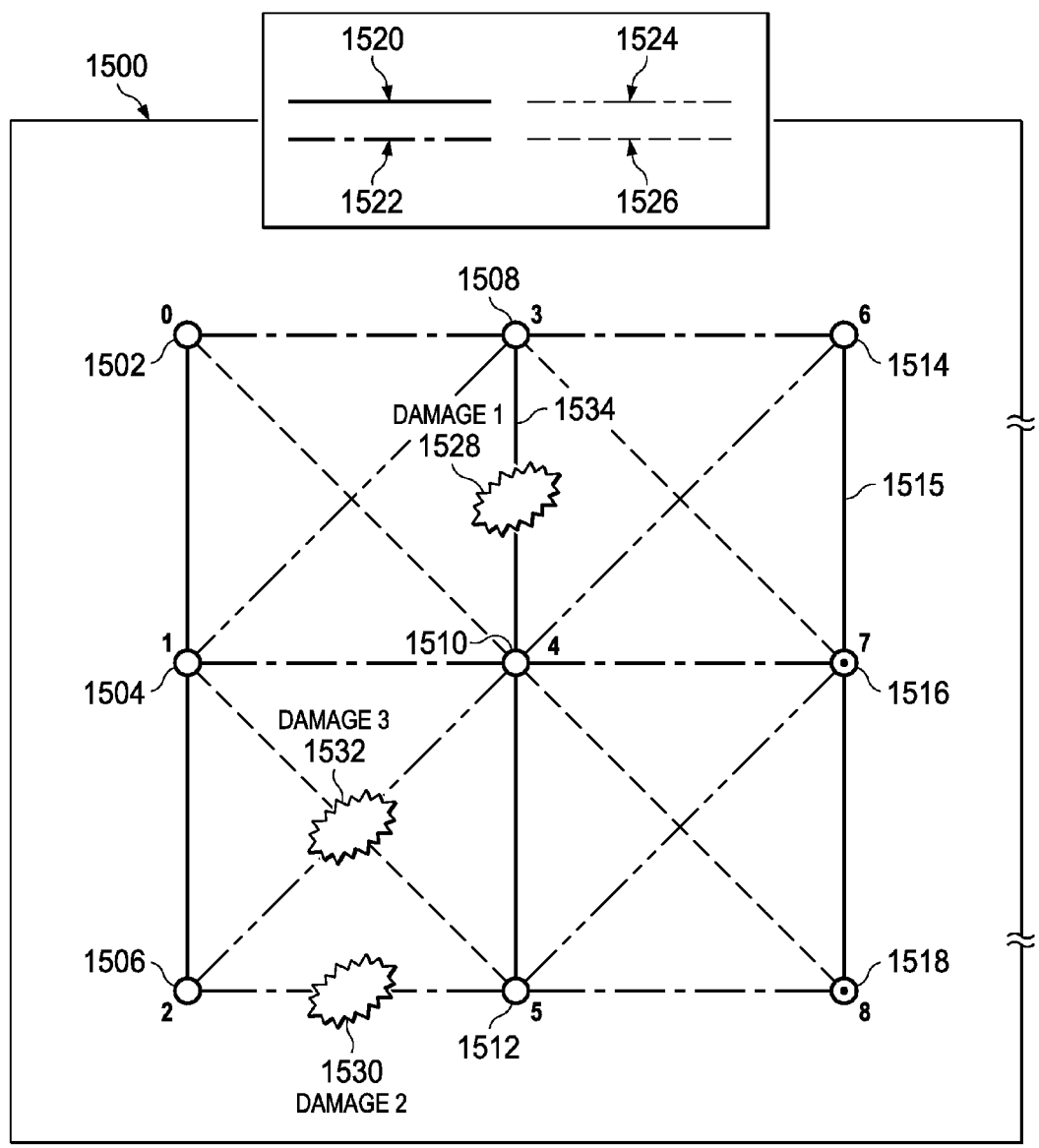
FIG. 15 is an illustration of a top view of an experimental setup on a portion of an object for testing for inconsistencies in the object in accordance with an advantageous embodiment.

With reference now to FIG. 15, an illustration of a top view of an experimental setup on a portion of an object for testing for inconsistencies in the object is depicted in accordance with an advantageous embodiment. In this illustrative example, object 1500 is an example of object 302 in FIG. 3 that may be tested for inconsistencies. Object 1500 is a composite skin panel in this illustrative example. In particular, object 1500 is a carbon fiber composite skin panel.

As depicted, transducer units 1502, 1504, 1506, 1508, 1510, 1512, 1514, 1516, and 1518 are placed on object 1500. These transducer units take the form of piezoelectric transducer (PZT) units. These transducer units are installed on surface 1515 of object 1500 in a square grid pattern having a spacing of about 15 centimeters.

In this illustrative example, transducer units 1502, 1504, 1506, 1508, 1510, 1512, 1514, 1516, and 1518 are arranged with substantially equal spacing. However, in other examples, these transducer units may have different distances from each other.

As depicted, various groups of paths may be formed by these transducer units. For example, groups 1520, 1522, 1524, and 1526 may be formed by the transducer units. In this illustrative example, each group only includes paths that are substantially equally spaced from other paths in the group and paths that have the same direction. Each group includes five paths. In this manner, a total number of 20 paths are formed by the transducer units.

Further, as depicted, object 1500 may have inconsistencies 1528, 1530, and 1532. Each of these inconsistencies may be, for example, a delamination of the composite skin panel. These inconsistencies may be located along some of the paths formed by the transducer units. For example, inconsistency 1528 is present along path 1534 in group 1520. These inconsistencies may be caused by undesired temperatures for object 1500.

Figure 16:
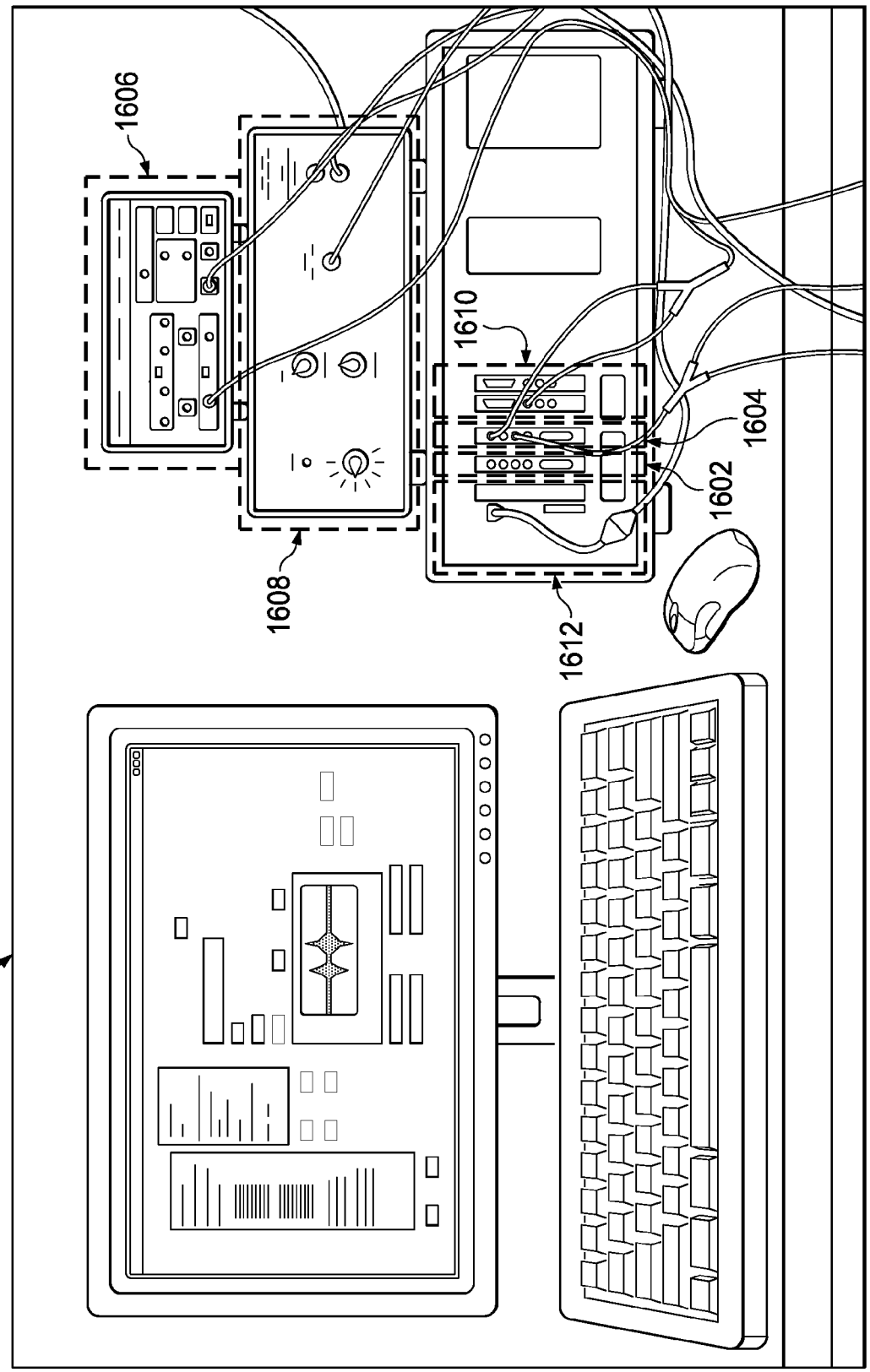
FIG. 16 is an illustration of a portion of a health monitoring system in accordance with an advantageous embodiment.

With reference now to FIG. 16, an illustration of a portion of a health monitoring system is depicted in accordance with an advantageous embodiment. In this illustrative example, health monitoring system 1600 is an example of one implementation for health monitoring system 304 in FIG. 3. Only a portion of health monitoring system 1600 is depicted in this illustrative example. Health monitoring system 1600 includes transducer units 1502, 1504, 1506, 1508, 1510, 1512, 1514, 1516, and 1518 in FIG. 15, but are not shown in this view.

As depicted, health monitoring system 1600 includes arbitrary waveform generator 1602, high speed signals digitizer 1604, low noise preamplifier 1606, power amplifier 1608, multiplexers 1610, and controller 1612. These components are used to generate signals that are transmitted in object 1500 in FIG. 15 by a first portion of transducer units 1502, 1504, 1506, 1508, 1510, 1512, 1514, 1516, and 1518 in FIG. 15 and detected and measured by a second portion of these transducer units. These signals are sent into object 1500 to identify the effects of inconsistencies 1528, 1530, and 1532 on Lamb wave modes.

With reference now to FIG. 17, an illustration of a graph comparing extracted asymmetric modes for a group of paths is depicted in accordance with an advantageous embodiment. In this illustrative example, graph 1700 includes horizontal axis 1702 and vertical axis 1704. Horizontal axis 1702 is time in milliseconds. Vertical axis 1704 is normalized amplitude for the asymmetric modes.

As depicted, curves 1706 are for the asymmetric modes extracted for a group of paths. These asymmetric modes may be extracted using the process illustrated in FIG. 13, for example. The asymmetric modes are extracted from signals traveling along paths in group 1520 at a temperature of about 50 degrees Celsius.

In this illustrative example, curves 1706 are for the asymmetric modes for paths in group 1520 in FIG. 15. In particular, curves 1706 are for group 1520 before any inconsistencies are present for object 1500. More specifically, curves 1706 are for group 1520 before inconsistency 1528 is present along path 1534 in FIG. 15.

As depicted, the arrival times for the asymmetric modes are substantially the same. In other words, in this illustrative example, a time delay is not present along the paths in group 1520 when an inconsistency is not present along the paths in group 1520.

With reference now to FIG. 18, an illustration of a graph comparing extracted asymmetric modes for a group of paths is depicted in accordance with an advantageous embodiment. In this illustrative example, curves 1706 in graph 1700 are for the asymmetric modes extracted for the paths in group 1520 in FIG. 15 when inconsistency 1528 is present along path 1534.

As depicted, the presence of inconsistency 1528 along path 1534 causes curve 1800 for the asymmetric mode extracted for path 1534 to be shifted to the right of the other curves in curves 1706. In other words, the arrival time for the asymmetric mode for path 1534 is delayed as compared to the arrival times for the other asymmetric modes for the other paths in group 1520. In this manner, the time delay identified using the asymmetric modes provides an indicator of the presence of an inconsistency.

With reference now to FIG. 19, an illustration of a portion of the charts identifying index values for paths is depicted in accordance with an advantageous embodiment. In this illustrative example, graphs 1900 provide an indication of which paths in the paths formed by transducer units 1502, 1504, 1506, 1508, 1510, 1512, 1514, 1516, and 1518 in FIG. 15 have inconsistencies present along the paths.

Graphs 1900 have horizontal axes 1902 and vertical axes 1904. The horizontal axes are identifiers for index values calculated using cross-correlation. For example, these index values may be calculated in operation 1400 in FIG. 14. The identifiers for the index values range from 1 to 20 because each index value is for a particular path in the 20 paths formed by transducer units 1502, 1504, 1506, 1508, 1510, 1512, 1514, 1516, and 1518 in FIG. 15.

Further, the index values are arranged in ascending order such that the first index value is the smallest index value and the twentieth index value is the twentieth smallest index value or the largest index value. In this illustrative example, charts for only some of the index values for the paths are depicted.

Inconsistencies are identified as being present along a path when an index value is greater than a threshold. This threshold is calculated each time a new index value is taken into consideration.

As depicted, in this illustrative example, inconsistencies are identified as being present along the paths corresponding to seventeenth smallest index value 1906, eighteenth smallest index value 1908, nineteenth smallest index value 1910, and twentieth smallest index value 1912.

With reference now to FIG. 20, an illustration of a table containing the results of testing an object for inconsistencies under different conditions is depicted in accordance with an advantageous embodiment. In this illustrative example, table 2000 contains the results of testing object 1500 in FIG. 15 for inconsistencies under various conditions.

Case 1 2002 is the test case for when inconsistencies are not present in object 1500. Case 2 2004 is the test case for when only one inconsistency, such as inconsistency 1528 in FIG. 15, is present in object 1500. Case 3 2006 is the test case for when two inconsistencies, such as inconsistency 1528 and inconsistency 1530 in FIG. 15, are present in object 1500. Case 4 2008 is the test case for when three inconsistencies, such as inconsistency 1528, inconsistency 1530, and inconsistency 1532 in FIG. 15, are present in object 1520.

Inconsistency locations 2010 identify the number of locations at which inconsistencies have been introduced in object 1500 for each case. Temperature 2012 identifies the different temperatures at which the different cases were tested.

Threshold value 2014 identifies the threshold value at which a first path corresponding to an index value is identified as having an inconsistency when the index values are arranged in the ascending order. Path and index value 2016 identify the particular paths with corresponding index values for which inconsistencies are identified as being present along the path.

As indicated by the data presented in table 2000, the method used for identifying inconsistencies in object 1500 accurately identifies inconsistency 1528, inconsistency 1530, and/or inconsistency 1532 at various temperatures. In particular, these inconsistencies are identified even at high temperatures, up to about 50 degrees Celsius, and low temperatures, up to about negative 10 degrees Celsius.

Figure 21:
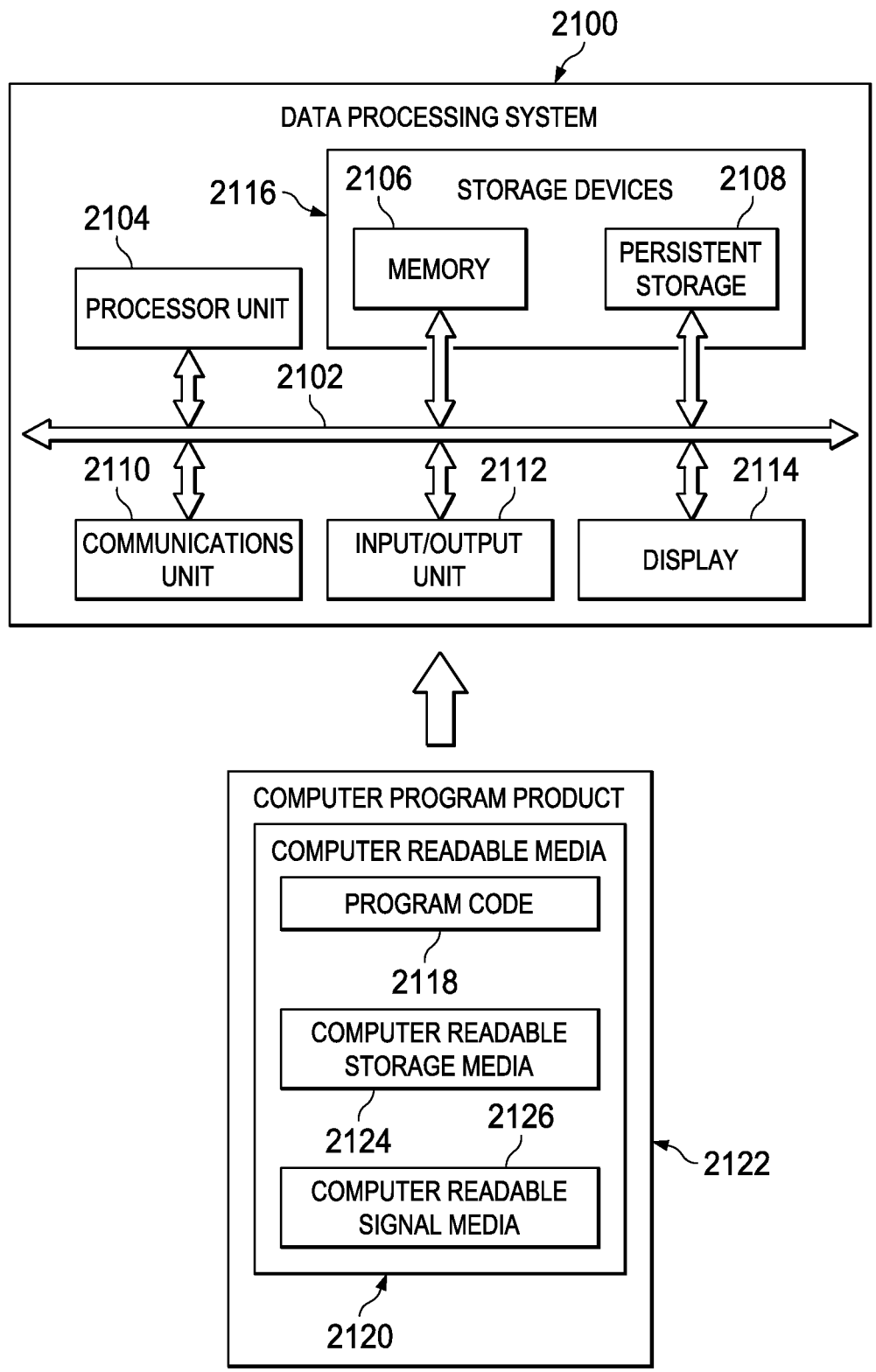
FIG. 21 is an illustration of a data processing system in accordance with an advantageous embodiment.

Turning now to FIG. 21, an illustration of a data processing system is depicted in accordance with an advantageous embodiment. In this illustrative example, data processing system 2100 may be used to implement one or more of number of computers 314 in FIG. 3. As depicted, data processing system 2100 includes communications fabric 2102, which provides communications between processor unit 2104, memory 2106, persistent storage 2108, communications unit 2110, input/output (I/O) unit 2112, and display 2114.

Processor unit 2104 serves to execute instructions for software that may be loaded into memory 2106. Processor unit 2104 may be a number of processors, a multi-processor core, or some other type of processor, depending on the particular implementation. A "number", as used herein with reference to an item, means "one or more items." Further, processor unit 2104 may be implemented using a number of heterogeneous processor systems in which a main processor is present with secondary processors on a single chip. As another illustrative example, processor unit 2104 may be a symmetric multi-processor system containing multiple processors of the same type.

Memory 2106 and persistent storage 2108 are examples of storage devices 2116. A storage device is any piece of hardware that is capable of storing information, such as, for example, without limitation, data, program code in functional form, and/or other suitable information either on a temporary basis and/or a permanent basis. Storage devices 2116 may also be referred to as computer readable storage devices in these examples. Memory 2106, in these examples, may be, for example, a random access memory or any other suitable volatile or non-volatile storage device. Persistent storage 2108 may take various forms, depending on the particular implementation.

For example, persistent storage 2108 may contain one or more components or devices. For example, persistent storage 2108 may be a hard drive, a flash memory, a rewritable optical disk, a rewritable magnetic tape, or some combination of the above. The media used by persistent storage 2108 may also be removable. For example, a removable hard drive may be used for persistent storage 2108.

Communications unit 2110, in these examples, provides for communications with other data processing systems or devices. In these examples, communications unit 2110 is a network interface card. Communications unit 2110 may provide communications through the use of either or both physical and wireless communications links.

Input/output unit 2112 allows for input and output of data with other devices that may be connected to data processing system 2100. For example, input/output unit 2112 may provide a connection for user input through a keyboard, a mouse, and/or some other suitable input device. Further, input/output unit 2112 may send output to a printer. Display 2114 provides a mechanism to display information to a user.

Instructions for the operating system, applications, and/or programs may be located in storage devices 2116, which are in communication with processor unit 2104 through communications fabric 2102. In these illustrative examples, the instructions are in a functional form on persistent storage 2108. These instructions may be loaded into memory 2106 for execution by processor unit 2104. The processes of the different embodiments may be performed by processor unit 2104 using computer implemented instructions, which may be located in a memory, such as memory 2106.

These instructions are referred to as program code, computer usable program code, or computer readable program code that may be read and executed by a processor in processor unit 2104. The program code in the different embodiments may be embodied on different physical or computer readable storage media, such as memory 2106 or persistent storage 2108.

Program code 2118 is located in a functional form on computer readable media 2120 that is selectively removable and may be loaded onto or transferred to data processing system 2100 for execution by processor unit 2104. Program code 2118 and computer readable media 2120 form computer program product 2122 in these examples. In one example, computer readable media 2120 may be computer readable storage media 2124 or computer readable signal media 2126. Computer readable storage media 2124 may include, for example, an optical or magnetic disk that is inserted or placed into a drive or other device that is part of persistent storage 2108 for transfer onto a storage device, such as a hard drive, that is part of persistent storage 2108. Computer readable storage media 2124 may also take the form of a persistent storage, such as a hard drive, a thumb drive, or a flash memory that is connected to data processing system 2100. In some instances, computer readable storage media 2124 may not be removable from data processing system 2100. In these examples, computer readable storage media 2124 is a physical or tangible storage device used to store program code 2118 rather than a medium that propagates or transmits program code 2118. Computer readable storage media 2124 is also referred to as a computer readable tangible storage device or a computer readable physical storage device. In other words, computer readable storage media 2124 is a media that can be touched by a person.

Alternatively, program code 2118 may be transferred to data processing system 2100 using computer readable signal media 2126. Computer readable signal media 2126 may be, for example, a propagated data signal containing program code 2118. For example, computer readable signal media 2126 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some advantageous embodiments, program code 2118 may be downloaded over a network to persistent storage 2108 from another device or data processing system through computer readable signal media 2126 for use within data processing system 2100. For instance, program code stored in a computer readable storage medium in a server data processing system may be downloaded over a network from the server to data processing system 2100. The data processing system providing program code 2118 may be a server computer, a client computer, or some other device capable of storing and transmitting program code 2118.

The different components illustrated for data processing system 2100 are not meant to provide architectural limitations to the manner in which different embodiments may be implemented. The different advantageous embodiments may be implemented in a data processing system including components in addition to or in place of those illustrated for data processing system 2100. Other components shown in FIG. 21 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 2104 may take the form of a hardware unit that has circuits that are manufactured or configured for a particular use. This type of hardware may perform operations without needing program code to be loaded into a memory from a storage device or to be configured to perform the operations.

For example, when processor unit 2104 takes the form of a hardware unit, processor unit 2104 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. With this type of implementation, program code 2118 may be omitted because the processes for the different embodiments are implemented in a hardware unit.

In still another illustrative example, processor unit 2104 may be implemented using a combination of processors found in computers and hardware units. Processor unit 2104 may have a number of hardware units and a number of processors that are configured to run program code 2118. With this depicted example, some of the processes may be implemented in the number of hardware units, while other processes may be implemented in the number of processors.

In another example, a bus system may be used to implement communications fabric 2102 and may be comprised of one or more buses, such as a system bus or an input/output bus. Of course, the bus system may be implemented using any suitable type of architecture that provides for a transfer of data between different components or devices attached to the bus system.

Additionally, a communications unit may include a number of one or more devices that transmit data, receive data, or transmit and receive data. A communications unit may be, for example, a modem or a network adapter, two network adapters, or some combination thereof. Further, a memory may be, for example, memory 2106, or a cache, such as found in an interface and memory controller hub that may be present in communications fabric 2102.

Thus, the different advantageous embodiments provide a method and apparatus for detecting an inconsistency in an object. In one advantageous embodiment, a method for detecting an inconsistency in an object is provided. Signals sent on a plurality of paths in the object are received at a plurality of transducer units associated with the object. Time delays are identified for a number of modes in the signals received at the plurality of transducer units. A determination is made as to whether a time delay in the time delays for the number of modes in the signals has a difference from a number of other time delays for the number of modes that is greater than a desired amount.

The different advantageous embodiments provide a detection apparatus and process that does not rely on pre-existing data. In other words, baseline data for the object without inconsistencies is unnecessary. Thus, the storage space for baseline data and generating baseline data for an object at various temperatures and other environmental conditions also is unnecessary. As a result, the time and expense needed for monitoring an object may be reduced.

In one or more of the advantageous embodiments, inconsistencies are detected without any comparison with previously obtained baseline data. This type of identification of inconsistencies may be performed even in the presence of environmental variations, such as, for example, without limitation, temperature, pressure, and/or other environmental changes. In some advantageous embodiments, velocities are identified from signals sent through an object during a current state for a structure. These velocities are used to determine whether an inconsistency is present in the object. Baseline or other comparisons formed at prior times based on different environmental conditions are not used. As a result, the identification of an inconsistency is not affected by environmental conditions.

The description of the different advantageous embodiments has been presented for purposes of illustration and description, and is not intended to be exhaustive or limited to the advantageous embodiments in the form disclosed. Many modifications and variations will be apparent to those of ordinary skill in the art.

Further, different advantageous embodiments may provide different advantages as compared to other advantageous embodiments. The advantageous embodiment or embodiments selected are chosen and described in order to best explain the principles of the advantageous embodiments, the practical application, and to enable others of ordinary skill in the art to understand the disclosure for various advantageous embodiments with various modifications as are suited to the particular use contemplated.

What is claimed is:

1. A method for detecting an inconsistency in an object, the method comprising:
   receiving signals sent on a plurality of paths in the object at a plurality of transducer units associated with the object;
   identifying time delays for a number of modes in the signals received at the plurality of transducer units; and
   determining whether a time delay in the time delays for the number of modes in the signals has a difference from a number of other time delays for the number of modes that is greater than a desired amount.

2. The method of claim 1, wherein the determining step comprises:
   determining whether an inconsistency is present based on whether the time delay in the time delays for the number of modes in the signals has the difference from the number of other time delays for the number of modes that is greater than the desired amount.

3. The method of claim 1 further comprising:
   identifying a path in the plurality of paths corresponding to the time delay as having an inconsistency in response to the time delay having the difference that is greater than the desired amount.

4. The method of claim 1, wherein the identifying step comprises:
   identifying velocities for the number of modes in the signals received at the plurality of transducer units, wherein a comparison of the velocities with each other is used to identify the time delays; and
   wherein the determining step comprises:
   determining whether a velocity in the velocities for the number of modes in the signals has a difference from other velocities in the velocities that is greater than the desired amount.

5. The method of claim 4, wherein the determining step comprises:
   performing a statistical analysis for the velocities to form a plurality of index values; and
   determining whether the velocity in the velocities is an outlier.

6. The method of claim 1, wherein the signals are sent on the plurality of paths using the plurality of transducer units.

7. The method of claim 1, wherein the determining step comprises:
   generating an index value for the number of modes for each path in the plurality of paths to form a plurality of index values, wherein the index value provides an indication of the time delay corresponding to the each path;
   identifying a threshold value, wherein an inconsistency is identified as being present if the index value is greater than the threshold value;
   comparing the index value in the plurality of index values with the threshold; and
   identifying a set of index values that are greater than the threshold.

8. The method of claim 1, wherein a transducer unit in the plurality of transducer units is selected from one of a transducer having a first plurality of segments configured to receive particular signals received on a path in the plurality of paths and a second transducer having a second plurality of segments configured to send the particular signals received on the path in the plurality of paths.

9. The method of claim 1, wherein the number of modes are selected as a particular number of modes in which a longer time delay is present for a particular path when an inconsistency is present along the particular path as compared to when the inconsistency is absent from the particular path.

10. The method of claim 1, wherein the number of modes comprises an asymmetric mode and wherein the plurality of paths are substantially equally spaced apart relative to each other.

11. The method of claim 1, wherein the object is selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, a building, a skin panel, an engine, a fuselage, a wing, a rib, and a stringer.

12. The method of claim 1, wherein the plurality of paths has a same direction.

13. A health monitoring system comprising:
a plurality of transducer units configured to receive signals from an object; and
a signal analysis module configured to identify time delays for a number of modes in the signals received by the plurality of transducer units in which the signals are received on a plurality of paths in the object in which the plurality of transducer units is associated with the object; and determine whether a time delay in the time delays for the number of modes in the signals has a difference from a number of other time delays in the time delays for the number of modes in the signals that is greater than a desired amount.

14. The health monitoring system of claim 13, wherein the signal analysis module is further configured to determine whether an inconsistency is present based on whether the time delay in the time delays for the number of modes in the signals has the difference from the number of other time delays for the number of modes that is greater than the desired amount.

15. The health monitoring system of claim 13, wherein the signal analysis module is further configured to identify a path in the plurality of paths corresponding to the time delay as having an inconsistency in response to the time delay having the difference that is greater than the desired amount.

16. The health monitoring system of claim 13, wherein in being configured to identify the time delays for the number of modes in the signals, the signal analysis module is configured to identify velocities for the number of modes in the signals received at the plurality of transducer units, wherein a comparison of the velocities with each other is used to identify the time delays; and wherein in being configured to determine whether the time delay in the time delays for the number of modes in the signals has the difference from the number of other time delays in the time delays for the number of modes in the signals that is greater than the desired amount, the signal analysis module is configured to determine whether a velocity in the velocities for the number of modes in the signals has a difference from other velocities in the velocities that is greater than the desired amount.

17. The health monitoring system of claim 13, wherein in being configured to determine whether the time delay in the time delays for the number of modes in the signals has the difference from the number of other time delays in the time delays for the number of modes that is greater than the desired amount, the signal analysis module is configured to generate an index value for the number of modes for each path in the plurality of paths to form a plurality of index values, wherein the index value provides an indication of the time delay corresponding to the each path; identify a threshold value, wherein an inconsistency is identified as being present if the index value is greater than the threshold value; compare the index value in the plurality of index values with a threshold; and identify a set of index values that are greater than the threshold.

18. A health monitoring system of an aircraft, the health monitoring system comprising:
a transducer system associated with a number of structures in the aircraft; and
a signal analysis module configured to cause a first plurality of transducer units associated with the number of structures in the aircraft to send signals on a plurality of paths in an object; identify time delays for asymmetric modes in the signals received by a second plurality of transducer units in the transducer system; and determine whether a time delay in the time delays for the asymmetric modes in the signals has a difference from a number of other time delays for the asymmetric modes that is greater than a desired amount.

19. The health monitoring system of claim 18, wherein the signal analysis module is further configured to extract the asymmetric modes in the signals in which an asymmetric mode in the asymmetric modes is for a corresponding path in the plurality of paths and wherein in being configured to identify the time delays for the asymmetric modes in the signals, the signal analysis module is configured to identify index values for the plurality of paths using the asymmetric mode for the each path in which each index value is for a particular path in the plurality of paths.

20. The health monitoring system of claim 19, wherein in being configured to determine whether the time delay in the time delays for the asymmetric modes in the signals has the difference from the number of other time delays for the asymmetric modes that is greater than the desired amount, the signal analysis module is further configured to arrange the index values in an ascending order; perform a statistical analysis using the index values in the ascending order; and identify a first index value in the ascending order having a value greater than a threshold, wherein a path corresponding to the first index value and any paths corresponding to any index values greater than the first index value are identified as having an inconsistency.

* * * * *